United States Patent [19]

Bamber

[11] Patent Number: 5,620,430
[45] Date of Patent: Apr. 15, 1997

[54] ABSORBENT ARTICLE HAVING FLAPS AND ZONES OF DIFFERENTIAL EXTENSIBILITY

[75] Inventor: Jeffrey V. Bamber, Cincinnati, Ohio

[73] Assignee: The Procter & Gamble Company, Cincinnati, Ohio

[21] Appl. No.: 253,001

[22] Filed: Jun. 2, 1994

Related U.S. Application Data

[62] Division of Ser. No. 73,256, Jun. 7, 1993, Pat. No. 5,389,094, which is a continuation of Ser. No. 769,891, Oct. 1, 1991, abandoned.

[51] Int. Cl.$^6$ .............................. A61F 13/15; A61F 13/20
[52] U.S. Cl. ..................... 604/385.2; 604/373; 604/386
[58] Field of Search .................................. 604/358, 373, 604/385.1, 385.2, 386–387, 390, 392, 393

[56] References Cited

U.S. PATENT DOCUMENTS

| | | |
|---|---|---|
| 3,211,147 | 10/1965 | Pherson et al. . |
| 3,343,543 | 9/1967 | Glassman . |
| 3,397,697 | 8/1968 | Rickard . |
| 3,658,063 | 4/1972 | Schaar . |
| 3,885,568 | 5/1975 | Schaar . |
| 3,924,626 | 12/1975 | Lee et al. . |
| 3,929,134 | 12/1975 | Karami . |
| 3,938,523 | 2/1976 | Gilliland et al. . |
| 4,166,464 | 9/1979 | Korpman . |
| 4,285,343 | 8/1981 | McNair . |
| 4,327,732 | 5/1982 | Thinnes . |
| 4,496,359 | 1/1985 | Pigneul . |
| 4,517,714 | 5/1985 | Sneed et al. . |
| 4,589,876 | 5/1986 | Van Tilburg . |
| 4,596,570 | 6/1986 | Jackson et al. . |
| 4,597,759 | 7/1986 | Johnson . |
| 4,605,404 | 8/1986 | Sneider . |
| 4,608,047 | 8/1986 | Mattingly . |

(List continued on next page.)

FOREIGN PATENT DOCUMENTS

| | | |
|---|---|---|
| 76104512 | 8/1987 | China . |
| 79205822 | 4/1989 | China . |
| 79202379 | 5/1989 | China . |
| 0249924 | 12/1987 | European Pat. Off. . |
| 0335527 | 4/1989 | European Pat. Off. . |
| 0405403 | 6/1989 | European Pat. Off. . |
| 0330206A1 | 8/1989 | European Pat. Off. . |
| 0331018A1 | 9/1989 | European Pat. Off. . |
| 0426235A2 | 5/1991 | European Pat. Off. . |
| 0446818A2 | 9/1991 | European Pat. Off. . |
| 0511905A1 | 11/1992 | European Pat. Off. . |
| 564904 | 11/1932 | Germany . |
| 1491234 | 4/1969 | Germany . |
| 3319421 | 11/1984 | Germany . |
| 2118021 | 10/1983 | United Kingdom . |
| WO91/03999 | 4/1991 | WIPO . |

*Primary Examiner*—John G. Weiss
*Assistant Examiner*—P. Zuttarelli
*Attorney, Agent, or Firm*—Jeffrey V. Bamber; Steven W. Miller; Jacobus C. Rasser

[57] ABSTRACT

An absorbent article, such as a sanitary napkin, having flaps and zones of differential extensibility for relieving the stresses that develop in the flaps when the flaps are folded down along the edges of crotch of the wearer's undergarments is provided.

8 Claims, 12 Drawing Sheets

U.S. PATENT DOCUMENTS

| | | |
|---|---|---|
| 4,615,696 | 10/1986 | Jackson et al. . |
| 4,681,579 | 7/1987 | Toussant et al. . |
| 4,687,478 | 8/1987 | Van Tilburg . |
| 4,690,680 | 9/1987 | Higgins . |
| 4,701,171 | 10/1987 | Boland et al. . |
| 4,701,174 | 10/1987 | Johnson . |
| 4,701,178 | 10/1987 | Glaug . |
| 4,704,114 | 11/1987 | Wilson et al. . |
| 4,747,846 | 5/1988 | Boland et al. . |
| 4,756,709 | 7/1988 | Stevens . |
| 4,790,838 | 12/1988 | Pigneul et al. . |
| 4,795,455 | 1/1989 | Luceri et al. . |
| 4,834,739 | 5/1989 | Linker et al. . |
| 4,854,985 | 8/1989 | Soderlund et al. . |
| 4,857,067 | 8/1989 | Wood et al. . |
| 4,900,319 | 2/1990 | Richwine . |
| 4,900,320 | 2/1990 | McCoy . |
| 4,911,701 | 3/1990 | Mavinkurve . |
| 4,917,697 | 4/1990 | Osborn, III et al. . |
| 4,936,839 | 6/1990 | Molee et al. . |
| 4,940,462 | 7/1990 | Salerno . |
| 4,944,735 | 7/1990 | Mokry . |
| 5,080,658 | 1/1992 | Igaue et al. . |
| 5,092,860 | 3/1992 | Pigneul . |
| 5,151,092 | 9/1992 | Buell et al. . |
| 5,181,915 | 1/1993 | Smith . |
| 5,281,209 | 1/1994 | Osborn, III et al. . |
| 5,330,461 | 7/1994 | Leeker . |
| 5,344,416 | 9/1994 | Niihara . |
| 5,346,486 | 9/1994 | Osborn, III et al. . |
| 5,354,400 | 10/1994 | Lavash et al. . |
| 5,389,094 | 2/1995 | Lavash et al. . |

ABSORBENT ARTICLE HAVING FLAPS AND ZONES OF DIFFERENTIAL EXTENSIBILITY

This is a division of application Ser. No. 08/073,256, filed on Jun. 7, 1993, now U.S. Pat. No. 5,389,094, which was a continuation of application Ser. No. 07/769,891, filed on Oct. 1, 1991, now abandoned.

FIELD OF THE INVENTION

The present invention relates to absorbent articles such as sanitary napkins, adult incontinence devices, and the like. Still more particularly, the present invention concerns absorbent articles having flaps and zones of differential extensibility for relieving the stresses that develop in the flaps when the flaps are folded down and under a wearer's undergarment.

BACKGROUND OF THE INVENTION

All manner and variety of absorbent articles configured for the absorption of body fluids such as menses, urine, and feces are, of course, well known. Absorbent articles, particularly sanitary napkins, having wings or flaps are disclosed in the literature and are available in the marketplace.

Generally, the flaps extend laterally from a central absorbent means and are intended to be folded around the edges of the wearer's panties in the crotch region. Thus, the flaps are disposed between the edges of the wearer's panties in the crotch region and the wearer's thighs. Commonly, the flaps are provided with an attachment means for affixing the flaps to the underside of the wearer's panties.

The flaps serve at least two purposes. First, the flaps prevent exudates which otherwise would soil the edges of the wearer's panties from doing such. Second, the flaps help stabilize the napkin from shifting out of place, especially when the flaps are affixed to the underside of the panties.

Sanitary napkins having flaps of the various types are disclosed in U.S. Pat. No. 4,687,478, entitled "Shaped Sanitary Napkin With Flaps", which issued to Van Tilburg on Aug. 18, 1987, U.S. Pat. No. 4,608,047, entitled "Sanitary Napkin Attachment Means", which issued to Mattingly on Aug. 26, 1986, U.S. Pat. No. 4,589,876, entitled "Sanitary Napkin", which issued to Van Tilburg on May 20, 1986, U.S. Pat. No. 4,285,343, entitled "Sanitary Napkin", which issued to McNair on Aug. 25, 1981, U.S. Pat. No. 3,397,697, entitled "Disposable Sanitary Shield For Undergarments", which issued to Rickard on Aug. 20, 1968, and U.S. Pat. No. 2,787,271, entitled "Sanitary Napkin", which issued to Clark on Apr. 2, 1957.

While sanitary napkins having flaps are commonly viewed as providing better protection against soiling as compared to sanitary napkins without flaps, the flapped napkins commonly experience problems that keep them from being optimally effective. These problems generally result from the stresses exerted on such flaps when the sanitary napkins are worn.

When the flaps are folded down along the edges of the wearer's panties, stresses are created in the flaps. The stresses are especially high along the fold line at the edges of the wearer's panties where the flaps are bent from the bodyside of the panty to the underside of the panty. These stresses are caused by fitting a flap around the curved outline of a panty crotch. These stresses are magnified when a wearer sits or crouches because the edges of the panties are pulled outward against the flaps thus increasing the forces against this fold line. When the stresses become too high, the flaps may become detached from the panty and some portion of the aforementioned benefits of the flaps may be lost. In addition, even if the stresses are not sufficient to detach the flaps, they may still be sufficient to cause the flaps to bunch longitudinally inward. This effectively reduces the size of the flaps and the area of the wearer's undergarments that the flaps are able to cover. Thus, there is a commercial need for a way of eliminating or at least reducing the stresses that develop in the flaps when folded, so as to prevent them from becoming detached from the wearer's panties and losing ability to cover a given area of the panties.

A number of variations on the types of flaps described above have been presented in an attempt to solve various problems. U.S. Pat. No. 4,900,320 issued to McCoy on Feb. 13, 1990, discloses a sanitary napkin having flaps affixed at points inward from the longitudinal edge of the napkin. U.S. Pat. No. 4,911,701 issued to Mavinkurve on Mar. 27, 1990, discloses a sanitary napkin having elastic means for providing greater convex shape to the body-facing portion of the central absorbent and for enabling adhesive-free placement of the flaps of the napkin. U.S. Pat. No. 4,940,462 issued to Salerno on Jul. 10, 1990, discloses a sanitary napkin with longitudinally expandable flaps. A sanitary napkin having flaps with stress relief means in the form of a notch or a slit is described in U.S. Pat. No. 4,917,697 which issued to Osborn, III, et al. on Apr. 17, 1990. Although this latter sanitary napkin works quite well, the search for sanitary napkins having improved flaps has continued.

The stresses described above can also unduly limit the size of the flaps used with an absorbent article since the stresses are typically greater in products having large flaps (that is flaps having a relatively large longitudinal dimension). There is, thus, also a need for an improved stress relief means for relieving the stresses that develop in the flaps, that does not limit the size of the flaps that can be used.

Therefore, it is an object of the present invention to provide an absorbent article, such as a sanitary napkin, having flaps and zones of differential extensibility for relieving the stresses that develop in the flaps when they are folded down along the edges of the crotch of the wearer's undergarments and affixed to the underside of the undergarments.

It is an additional object of the present invention to provide an absorbent article having flaps and zones of differential extensibility that allow larger flaps to be used on the absorbent article, than those of prior products.

These and other objects of the present invention will be more readily apparent when considered in reference to the following description and when taken in conjunction with the accompanying drawings.

SUMMARY OF THE INVENTION

In accordance with the present invention, an absorbent article, such as a sanitary napkin, having flaps and zones of differential extensibility for relieving the stresses that develop in the flaps when the flaps are folded down along the edges of the wearer's panties in the crotch, is provided.

The sanitary napkin has a principal longitudinal centerline and a principal transverse centerline. The sanitary napkin comprises a main body portion and a pair of flaps associated with the main body portion. The main body portion of the sanitary napkin comprises a liquid pervious topsheet, a liquid impervious backsheet joined to the topsheet, an absorbent core positioned between the topsheet and the backsheet.

The main body portion has two spaced apart longitudinal edges and two spaced apart transverse edges.

The flaps extend laterally outward from the main body portion. The flaps are associated with the main body portion at a juncture along the longitudinal edges of the main body portion. The flaps are divided into a front half and a back half by a flap transverse centerline. The absorbent article has two corner regions located adjacent the area of the ends of the Junctures. One corner region is located adjacent the area of the juncture in each direction remote from the principal transverse centerline. The sanitary napkin comprises zones of differential extensibility which allow the corner regions to extend transversely outward to a greater degree than the portions of the sanitary napkin located along the flap transverse centerline. The zones of differential extensibility provide a means for the relief of stresses in the flaps of the sanitary napkin when the sanitary napkin is placed in the wearer's undergarments. A nonlimiting number of types of zones of differential extensibility are disclosed.

DETAILED DESCRIPTION OF PREFERRED EMBODIMENTS

Figure 1:
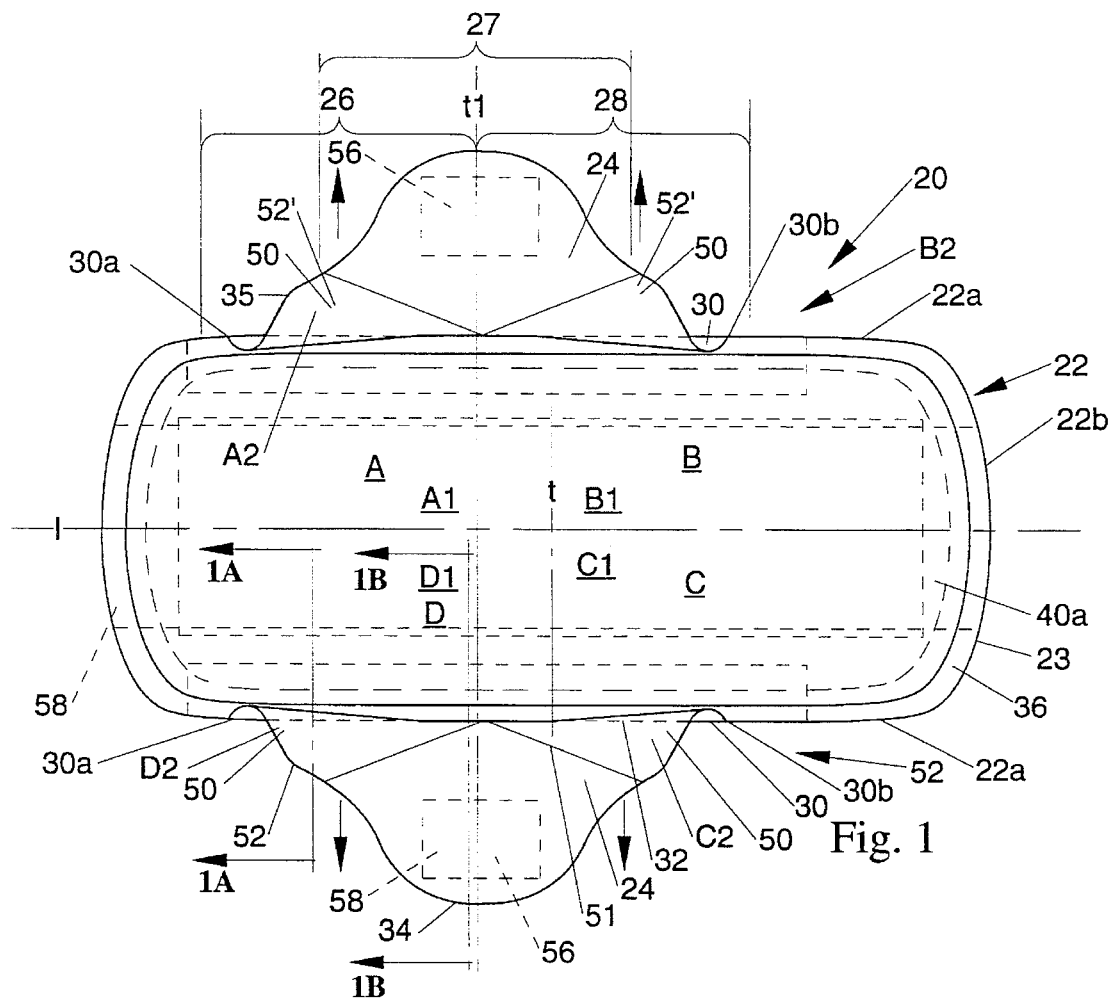
FIG. 1 is a top plan view of a preferred sanitary napkin embodiment of the present invention.

The present invention relates to absorbent articles, such as sanitary napkins. More particularly, the present invention relates to absorbent articles having flaps and zones of differential extensibility for relieving the stresses that develop in the flaps when they are folded down along the edges of the crotch of the wearer's undergarments and attached to the underside of the undergarments.

The term "absorbent article", as used herein, refers to articles which absorb and contain body exudates. More specifically, the term refers to articles which are placed against or in proximity to the body of the wearer to absorb and contain the various exudates discharged from the body. The term "absorbent article" is intended to include sanitary napkins, pantiliners, and incontinent pads (and other articles worn in the crotch region of a garment). The term "disposable" refers to articles which are intended to be discarded after a single use and preferably recycled, composted, or otherwise disposed of in an environmentally compatible manner. (That is, they are not intended to be laundered or otherwise restored or reused as an absorbent article.) In the preferred embodiment illustrated, the absorbent article is a sanitary napkin designated 20.

The term "sanitary napkin", as used herein, refers to an article which is worn by females adjacent to the pudendal region that is intended to absorb and contain the various exudates which are discharged from the body (e.g., blood, menses, and urine). The present invention, however, is not limited to the particular types or configurations of absorbent articles shown in the drawings.

A preferred embodiment of a sanitary napkin 20 of the present invention is shown in FIG. 1. As shown in FIG. 1, the sanitary napkin 20 basically comprises an absorbent means represented by central absorbent pad (or "main body portion") 22, and two flaps 24. (In the discussion that follows, unless otherwise noted, the sanitary napkin described herein will have two flaps. While it is not necessary that the napkin have two flaps, two flaps are preferred over one flap. Also, while it is not necessary that the flaps be mirror images of one another, they preferably are. Thus, the description of one flap will be a description of the other, and, for clarity, discussion of the second flap may be omitted.)

The sanitary napkin 20 has two centerlines, a principal longitudinal centerline 1 and a principal transverse centerline t. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction.

Figure 1A:
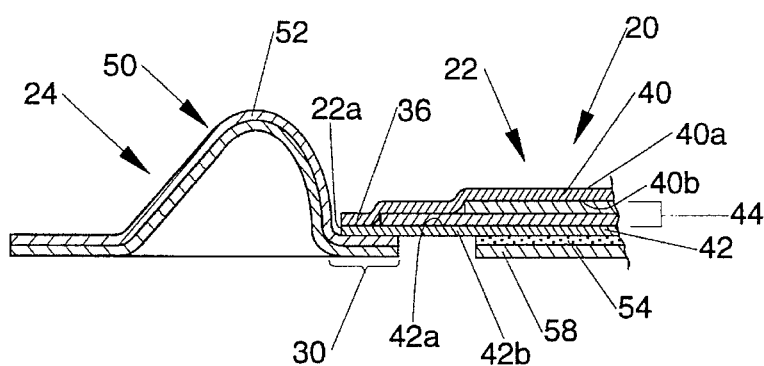
FIG. 1A is a lateral cross-sectional view taken along line 1A—1A of FIG. 1 through the corner region of one of the flaps of the sanitary napkin.
Figure 1B:
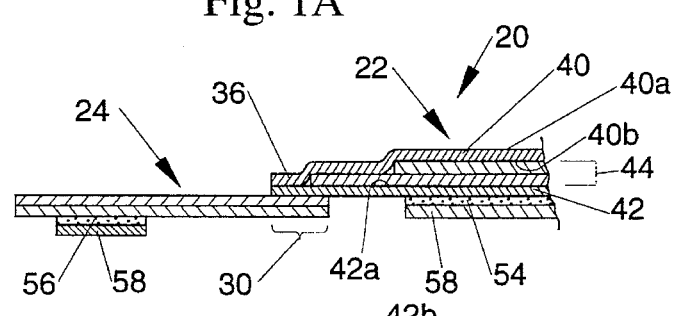
FIG. 1B is a lateral cross-sectional view taken along line 1B—1B of FIG. 1 through the center portion of one of the flaps.

The sanitary napkin 20 is comprised of a topsheet 40, a backsheet 42, an absorbent core 44, and a pair of flaps 24. At least a part of the topsheet 40, backsheet 42, and absorbent core 44 comprise the main body portion 22. The flaps 24 shown in FIGS. 1 and 1A are comprised of separate pieces of material which are attached to the main body portion 22. (In alternative embodiments, such as those shown in U.S. Pat. No. 4,917,697 issued to Osborn, the flaps 24 may be integral with the main body portion 22. In such a case, the topsheet 40 may form one surface of both the flaps 24 and the main body portion 22, and the backsheet 42 may form the other surface of the same. In addition, the absorbent material of the sanitary napkin 20 may extend into the flaps 24 to form a flap absorbent core, as described in greater detail in U.S. Pat. No. 4,917,697.)

The flaps 24 are each associated with main body portion 22 along a juncture. This is typically a longitudinally-oriented (or "longitudinal") juncture, such as lines of juncture 30. As used herein, the terms "juncture" (or "line of juncture") refer to regions where the flaps 24 extend from or are joined to the main body portion 22. These regions can be any of various curved or straight lines, but they are not limited to lines. Thus, these regions can comprise flanges, strips, intermittent lines, and the like. In the embodiment illustrated in FIG. 1, line of juncture 30 is a relatively straight line.

The flaps 24 have a proximal edge 32 adjacent the line of juncture. A distal edge (or "free end") 34 is remote from the line of juncture 30. As shown in FIG. 1, each flap 24 is divided into a front half 26, and a back half 28 by a flap transverse centerline $t_1$. The flap transverse centerline $t_1$ may coincide with the principal transverse centerline t of the sanitary napkin 20, but this is not absolutely required. The flap transverse centerline $t_1$ extends through the principal longitudinal centerline 1 to divide the sanitary napkin into four quarters A, B, C, and D.

The quarters comprise a first portion or zone (such as $A_1$, $B_1$, $C_1$, and $D_1$) adjacent at least a portion of the principal longitudinal centerline 1 and the flap transverse centerline $t_1$. A second portion or zone ($A_2$, $B_2$, $C_2$, and $D_2$) is outboard of and complementary with the first portion. (The terms "outboard" or "outward", as used herein, mean generally spaced in a direction away from these centerlines. The term "complementary", as used herein, means that the first and second portions form an entire quarter.)

The sanitary napkin 20 has at least one zone of differential extensibility (or "zone of extensibility", or simply "zone") 50. Preferably, as shown in FIG. 1, the sanitary napkin 20 has four zones of differential extensibility 50, one in each quarter of the sanitary napkin 20. The zones of differential extensibility 50 relieve the stresses which develop in the flaps 24 when they are folded around a panty crotch. Since the zones of differential extensibility 50 relieve stresses in the flaps, they may be referred to herein as a type of "stress relief means".

The term "zone of differential extensibility", as used herein, refers to a portion of the sanitary napkin 20 which is capable of extending a differing amount (preferably a greater amount), than surrounding portions of the sanitary napkin 20. These "surrounding portions" of the sanitary napkin comprise the first portions of the quarters. The zones of differential extensibility 50, thus, comprise the second portions of each quarter.

The zones of differential extensibility 50 are preferably primarily extensible in a greater amount generally outward in the transverse direction. This is generally in the direction of the arrows shown in FIG. 1. As used herein, "generally in the transverse direction" means that the extensibility has a transverse component. All of the extension, however, need not be exactly parallel to the principal transverse centerline of the sanitary napkin. The extensibility is preferably oriented more in the transverse direction than in the longitudinal direction.

The zone(s) of differential extensibility 50 can comprise any structure capable of extending a greater amount in the transverse direction than the surrounding portions of the sanitary napkin. The differential extensibility referred to herein, however, must be elasticless. That is, it must be accomplished without the use of separate elastic pieces, strands, or materials to contract one or more portions of the sanitary napkin. The zones of differential extensibility must also be accomplished without slitting or notching portions of the sanitary napkin that cover the wearer's undergarments. This will have the advantage that exudates will not be able to travel through the slits or notches to soil the wearer's undergarments.

Suitable structures for the zones of differential extensibility 50 include, but are not limited to zones of material that are mechanically strained, corrugated, "ring rolled", folded, pleated, or joined along a curved juncture. These structures (although sometimes shown only as being part of the flaps 24), can comprise portions of the main body portion 22, portions of the flaps 24, or both. They can be integral parts of these components of the sanitary napkin, or separate elements, such as pieces of material, joined to the sanitary napkin.

The zones of differential extensibility 50 are more specifically located in the corner regions 52 of the sanitary napkin 20. (Thus, the second portions $A_2$, $B_2$, $C_2$, and $D_2$ of the quarters preferably comprise the corner regions 52 of the sanitary napkin 20.) The sanitary napkin 20 preferably has four corner regions 52 (two by each flap, and one in each quarter).

The term "corner regions" 52, as used herein, refers to portions of the sanitary napkin 20 that are generally located along or adjacent a portion of the longitudinal juncture of each flap 24. The corner regions 52 for each flap 24 are located in two areas in the regions of the ends 30a and 30b of each Juncture 30. One corner region 52 is located adjacent the longitudinal juncture 30 in the front half 26 of the flap 24. The other is adjacent the longitudinal Juncture 30 in the back half 28 of the flap 24. The corner regions 52 are preferably at least partially disposed longitudinally away from the flap transverse centerline $t_1$ in each direction. (Thus, the corner regions 52 may be described as being longitudinally "remote" from the flap transverse centerline $t_1$.)

In the most preferred case (as will be subsequently described in greater detail), the zones of differential extensibility 50 are located along a portion of the fold line where the flaps 24 are folded around the wearer's panty crotch. The fold line will typically be located along or adjacent the longitudinal juncture 30 of each flap 24. Since the terms "portions", "zones", and "regions", as used herein, refer to general areas, the zones of differential extensibility 50 and the corner regions 52 are, thus, not limited to points which lie precisely on the lines of juncture 30. Typically, they will include both those points which lie on the lines of juncture 30 as well as the surrounding areas of the sanitary napkin 20 (which include the aforementioned fold lines). The longitudinal junctures, thus, typically serve as good approximations for the location of the zones of differential extensibility 50.

The corner regions 52 are designated as such because they typically include the "corners" formed along the periphery 23 of the sanitary napkin 20. The "corners" occur where the edges 35 of the flaps 24 intersect with the longitudinal side edges 22a of the main body portion 22 when the sanitary napkin 20 is shown in a plan view. It is not necessary for there to be a sharp angle formed at the intersect ion of these edges, or for lines of demarcation to designate the same, however. (Another way to describe the corner regions 52 is with reference to U.S. Pat. No. 4,917,697 issued to Osborn, III, et al. The corner regions 52 described herein are typically comprised at least of those areas shown as having slits or notches in the Osborn, et al. patent. (For simplicity, these areas may be referred to herein as "notch regions"). However, the corner regions 52 in the present invention preferably encompass a larger area than the slits or notches shown in the Osborn patent.)

The portions of the flaps 24 in the corner regions 52 of the sanitary napkin 20 may be referred to as the "corner regions of the flaps" or "flap corner regions". These may be separately designated 52' although they are still considered to comprise the corner regions 52, per se.

FIGS. 1 and 1A show an embodiment of the present invention which has one preferred type of zones of differential extensibility 50. In the embodiment shown in FIGS. 1 and 1A, the zones of differential extensibility 50 comprise portions of the sanitary napkin 20 that have slack provided therein. These portions of the sanitary napkin 20 comprise at least the flap corner regions 52'.

The slack is provided to the sanitary napkin 20 in the embodiment shown in FIGS. 1 and 1A by pre-stretching (or "pre-straining") the corner regions of the flaps 52'. This can be accomplished by heating and then stretching the flap corner regions generally in the transverse direction. This heating and stretching increases the size of the flap corner regions 52'. Thus, when the sanitary napkin is laid out as shown in FIGS. 1 and 1A with the flaps 24 extended, there is excess material in the flap corner regions 52'. This excess material (as described in greater detail below) allows the flaps 24 to be folded around the crotch of the wearer's panties without stresses being created in the corner regions 52.

Any known method of stretching materials can be used to pre-stretch the corner regions 52. (It is expressly not admitted, however, that the use of zones of differential extensibility 50 in the manner of the present invention is known.) Any suitable process that stretches the material of the corner regions 52 beyond their point of plastic deformation to permanently deform (or elongate) the corner regions 52 can be used. For instance, it is not necessary for the corner regions 52 to be heated prior to stretching the same. Heating may make the stretching easier, however. In addition to pre-stretching, a number of alternative ways of providing zones of differential extensibility are described in greater detail below in conjunction with the embodiments shown in the remaining drawing figures.

The individual components of the sanitary napkin 20 will first be looked at in greater detail.

The topsheet 40 is liquid permeable and when the sanitary napkin 20 is in use, the topsheet 40 is in close proximity to the skin of the user. The topsheet 40 is compliant, soft feeling, and non-irritating to the user's skin. It can be made from any of the materials conventional for this type of use. Nonlimiting examples of suitable materials that can be used as topsheet 40 are woven and nonwoven polyester, polypropylene, nylon, and rayon and formed thermoplastic films, with formed films being preferred.

Suitable formed films are described in U.S. Pat. No. 3,929,135, entitled "Absorptive Structure Having Tapered Capillaries", which issued to Thompson on Dec. 30, 1975, U.S. Pat. 4,324,426, entitled "Disposable Absorbent Article Having A Stain-Resistant Topsheet", which issued to Mullane and Smith on Apr. 13, 1982, U.S. Pat. No. 4,342,314, entitled "Resilient Plastic Web Exhibiting Fiber-Like Properties", which issued to Radel and Thompson on Aug. 3, 1982, and U.S. Pat. No. 4,463,045, entitled "Macroscopically Expanded Three-Dimensional Plastic Web Exhibiting Non-Glossy Visible Surface and Cloth-Like Tactile Impression", which issued to Ahr, Louis, Mullane, and Ouellette on Jul. 31, 1984. Formed films are preferred for topsheet 40 because they are pervious to liquids and yet non-absorbent. Thus, the surface of the formed film which is in contact with the body remains dry and is more comfortable to the wearer.

In one particularly preferred embodiment (shown in FIG. 14 without the zones of differential extensibility of the present invention) the sanitary napkin 20 is comprised of components that are extensible (i.e., capable of stretching, particularly in the longitudinal direction) when the sanitary napkin is worn. Preferably, the sanitary napkin 20 is capable of elongating between about 15% and about 40% of its unstretched length. This extensibility provides better in-use fit, comfort, and decreased staining. In other embodiments, only limited portions of the components of the sanitary napkin 20 are capable of stretching.

A particularly preferred topsheet 40 for use in such an embodiment is one which is made in accordance with U.S. Pat. No. 4,463,045 and ring rolled to provide it with a degree of longitudinal extensibility. Suitable processes for ring rolling or "pre-corrugating" are described in U.S. Pat. No. 4,107,364 issued to Sisson on Aug. 15, 1978. U.S. Pat. No. 4,834,741 issued to Sabee on May 30, 1989 and in co-pending, commonly assigned U.S. patent application Ser. No. 07/662,536 entitled "Improved Method And Apparatus For Incrementally Stretching A Zero Strain Stretch Laminate Web To Impart Elasticity Thereto" filed by Gerald M. Weber et al. on Feb. 28, 1991, U.S. patent application Ser. No. 07/662,537 entitled "Improved Method and Apparatus For Incrementally Stretching Zero Strain Stretch Laminate Web In A Non-Uniform Manner To Impart A Varying Degree of Elasticity Thereto" filed by Kenneth B. Buell et al. on Feb. 28, 1991, and U.S. patent application Ser. No. 07/662,543 entitled "Improved Method And Apparatus For Sequentially Stretching Zero Strain Stretch Laminate Web To Impart Elasticity Thereto Without Rupturing The Web" filed by Gerald M. Weber et al. on Feb. 28, 1991. The fold lines in the corrugations of the topsheet should run in the transverse direction so the topsheet is longitudinally extensible.

Such a topsheet is described in greater detail in the following patent applications which were filed on Jun. 23, 1991: U.S. patent application Ser. No. 07/734,404 entitled "Absorbent Articles, Especially Catamenials, Having Improved Fluid Directionality, Comfort and Fit" filed in the names of Thompson, et al.; U.S. patent application Ser. No. 07/734,392 entitled "Fluid Handling Structure for Use in Absorbent Articles" filed in the names of Thompson, et al.; and, U.S. patent application Ser. No. 07/734,405 entitled "Absorbent Core for Use in Catamenial Products" filed in the names of Buenger, et al. These patent applications may be referred to collectively as the "Capillary Channel Fiber" patent applications.

In addition, in preferred embodiments of the present invention, at least a portion of the outer surface 40a of the topsheet 40 is treated with a surfactant. It is preferred that the surfactant be substantially evenly and completely distributed across at least the portion of the outer surface 40a of topsheet 40 that overlays the main body portion 22. This can be accomplished by any of the common techniques well known to those skilled in the art. For example, the surfactant can be applied to topsheet 40 by spraying, by padding, or by the use of transfer rolls.

Treating the outer surface 40a of the topsheet 40 with a surfactant renders the surface of the topsheet 40 more hydrophilic. This results in liquid penetrating the topsheet 40 faster than it would if the surface were not treated. This diminishes the likelihood that menstrual fluids will flow off topsheet 40 rather than being absorbed by the absorbent core 44. Preferably, any portions of the topsheet 40 that overlay the flaps 24 are not treated with the surfactant. This will minimize any tendencies fluids may have to spread laterally across the flaps and to come in contact with the wearer's thighs and other parts of the wearer's body.

In preferred embodiments, the inner surface 40b of topsheet 40 is secured in contacting relation with the absorbent core 44. This contacting relationship results in liquid penetrating topsheet 40 faster than if the topsheet 40 were not in contact with absorbent core 44. The topsheet 40 can be maintained in contact with absorbent core 44 by applying adhesive to the inner surface 40b of the topsheet 40. Suitable adhesives useful for this purpose are described in U.S. Pat. No. 4,917,697. The adhesives can be applied by the same methods as the surfactant is applied to the outer surface 40a of the topsheet 40.

The absorbent core 44 is positioned between the topsheet 40 and the backsheet 42. The absorbent core 44 provides the means for absorbing menstrual fluid. The absorbent core 44 need not have an absorbent capacity much greater than the total amount of menstrual fluid anticipated to be absorbed. The absorbent core 44 is generally compressible, conformable, and non-irritating to the user's skin. It can comprise any material used in the art for such purpose. Examples include comminuted wood pulp which is generally referred to as airfelt, creped cellulose wadding, absorbent foams, absorbent sponges, synthetic staple fibers, polymeric fibers, hydrogel-forming polymer gelling agents, peat moss, or any equivalent material or combinations of materials.

Polymeric gelling agents are those materials which, upon contact with fluids (i.e., liquids) such as water or body fluids, imbibe such fluids and thereby form hydrogels. In this manner, fluids discharged into the absorbent core 44 can be acquired and held by the polymeric gelling agent, thereby providing the articles herein with enhanced absorbent capacity and/or improved fluid retention performance.

The polymeric gelling agent which is employed in the absorbent core 44 will generally comprise particles of a substantially water-insoluble, slightly cross-linked, partially neutralized, hydrogel-forming polymer material. The term "particles", as used herein, can refer to particles in any form, such as in the form of pellets, flakes, or fibers. The characteristics of the absorbent core 44 (including, but not limited to the preferred types of polymer materials used therein, and types of methods which can be used for preparing these polymer particles) are described in greater detail in U.S. Pat. No. 5,009,653 issued to Osborn and the patents incorporated by reference in that patent, the disclosures of which are all incorporated by reference herein.

In one preferred embodiment, the absorbent core 44 is a laminate comprised of a layer of superabsorbent polymer material, such as in the form of particles, disposed between two air-laid tissues, first and second tissue layers (or "upper" and "lower" tissue layers). The first and second tissue layers provide containment of the superabsorbent polymer material, improve lateral wicking of the absorbed exudates throughout the absorbent core 44 and provide a degree of absorbency.

A suitable laminate is the superabsorbent laminate WATER-LOCK L-535 available from the Grain Processing Corporation of Muscatine, Iowa (WATER-LOCK registered TM by Grain Processing Corporation). Such superabsorbent laminates are disclosed in U.S. Pat. No. 4,467,012, entitled "Composition For Absorbent Film And Method Of Preparation", which issued to Pedersen et al. on Aug. 21, 1984, and U.S. Pat. No. 4,260,443, entitled "Laminated Absorbent Process", which issued to Lindsay et al. on Apr. 7, 1981.

Figure 14:
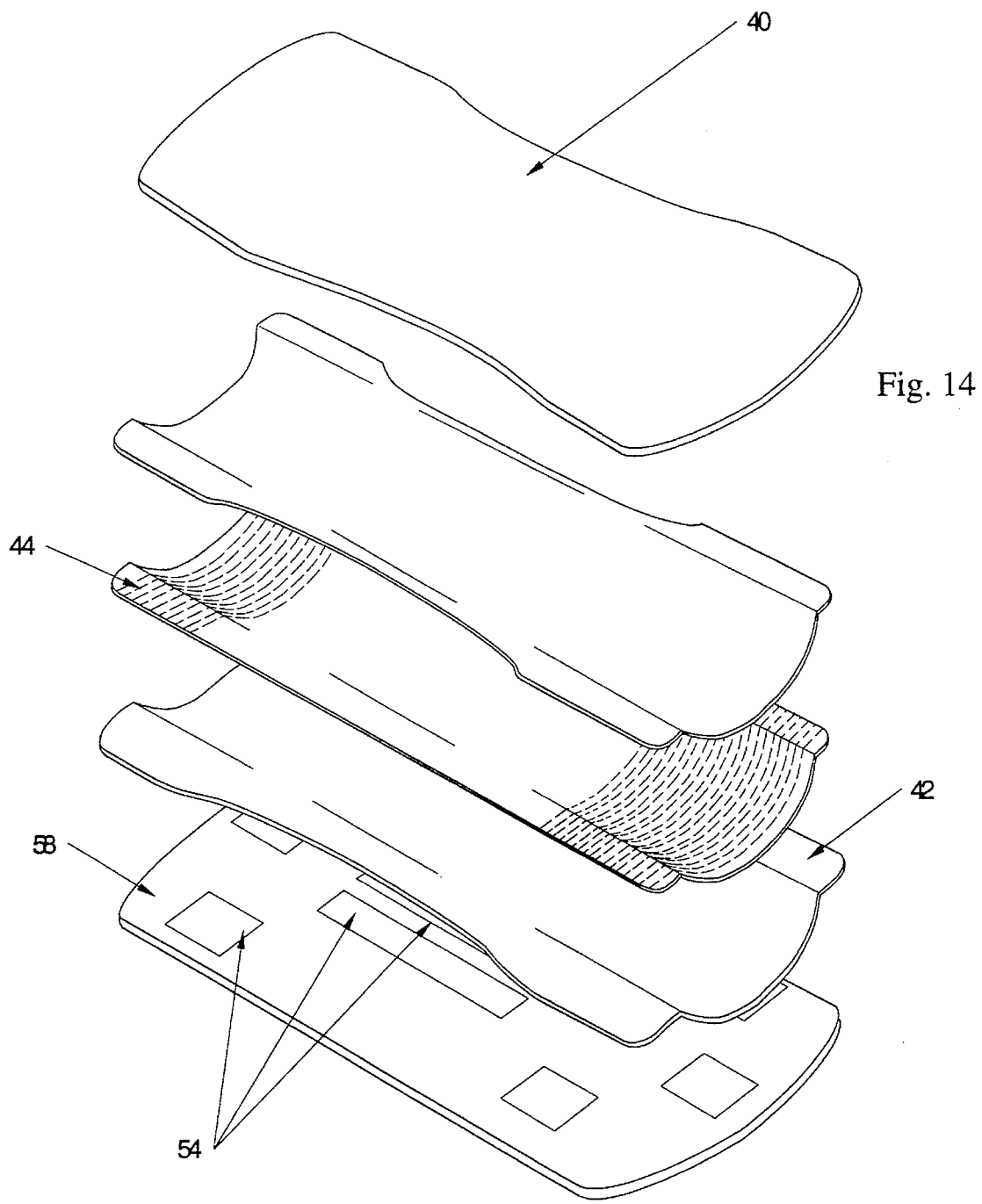
FIG. 14 is an exploded perspective view showing the assembly of a sanitary napkin which contains a preferred absorbent core and panty fastening adhesive pattern for use in the present invention (but which does not include flaps and the zones of differential extensibility of the present invention).

In a particularly preferred embodiment, the absorbent core 44 is a laminate as described above which is slitted or partially slitted for longitudinal extensibility as shown in FIG. 14 in the accompanying drawing figures. This slitted or partially slitted core is described in greater detail in the Capillary Channel Fiber patent applications.

The backsheet 42 is impervious to liquids and, thus, prevents menstrual fluid from soiling the clothing of the user. Any material used in the art for such purpose can be utilized herein. Suitable materials include embossed or non-embossed polyethylene films and laminated tissue. A suitable polyethylene film is manufactured by Monsanto Chemical Corporation and marketed in the trade as Film No. 8020.

In one alternative embodiment of the sanitary napkin 20 (typically in which the topsheet 40 overlays only the main body portion 22 and does not extend out to form the top surface of the flaps), the backsheet 42 may be comprised of two layers. In such a case, the backsheet 42 may comprise a first layer of lofted material disposed on the core-facing side 42a of the backsheet. The purpose of the first layer is to provide a comfortable, non-irritating surface against the body of the wearer. The lofted layer may be comprised of any suitable material, such as a nonwoven material. Preferably, the lofted layer comprises a hydrophobic nonwoven material. The second layer may be disposed on the garment side 42b of the backsheet 42, and may comprise a fluid impervious film. A low density polyethylene material about 0.01 to about 0.05 millimeters in thickness, preferably about 0.02 millimeters in thickness, has been found to work well as this second layer. A polyethylene film, such as is sold by the Ethyl Corporation, Visqueen Division, under model XP-39385 has been found particularly well suited for this second layer. The backsheet 42 may also be made of a soft, cloth-like material which is hydrophobic relative to the topsheet 40. A polyester or polyolefinic fiber backsheet 42 has been found to work well. A particularly preferred soft, cloth-like backsheet 42 material is a laminate of a polyester nonwoven material and a film such as described in U.S. Pat. No. 4,476,180 issued to Wnuk on Oct. 9, 1984.

A particularly preferred extensible backsheet 42 is an extended adhesive film Formula #198-338 manufactured by the Findley Adhesives Company of Wauwatosa, Wis. which is described in greater detail in the Capillary Channel Fiber patent applications.

As shown in FIGS. 1 and 1A, the topsheet 40 is secured to backsheet 42 along a first seam, such as seam 36. The seam 36 can be formed by any means commonly used in the art for this purpose such as by gluing, crimping, or heat-sealing. The seam 36 is illustrated In FIG. 1 as extending completely around the periphery of the math body portion 22. This is a preferred embodiment for ease of construction. (Other means of uniting the various elements can be used.)

The main body portion 22 is the portion of the sanitary napkin 20 that contains an absorbent means, such as absorbent core 44. The main body portion 22 has a liquid pervious body contacting surface (represented in FIG. 1A by topsheet 40) and an opposed liquid impervious surface (represented in FIG. 1A by backsheet 42). It is to be understood that the embodiment illustrated is only one possible embodiment, albeit a preferred one. Other possible embodiments include one in which an absorbent core 44 is essentially completely wrapped with topsheet before it is placed on a backsheet. The main body portion 22 can also comprise an absorbent core which possesses sufficient integrity to stand alone and is liquid pervious on one surface while the other surface has been treated to render it liquid impervious.

The main body portion 22 may be relatively thick or relatively narrow and thin. A narrow main body portion 22 may be effective because the overall configuration and use of sanitary napkin 20 results in main body portion 22 being maintained in close proximity to the body. Such proximity of main body portion 22 places it precisely where it should be: very near the body at the vaginal opening. The main body portion 22 can then absorb the vast majority of the menstrual fluid (menses) before it has an opportunity to flow along the sides of the main body portion 22. A thin main body portion may also be desired because it is typically comfortable to the user.

FIGS. 1 and 1A also show the fasteners, such as adhesive attachment means, central pad adhesive 54 and flap adhesive 56, which are adapted to secure the sanitary napkin 20 to the crotch region of an undergarment.

The central pad adhesive 54 provides an adhesive attachment means for securing main body portion 22 in the crotch portion of a panty. The outer surface of flap 24, adjacent the distal edge 34 of the flap, is preferably coated with a flap adhesive 56. The flap adhesive 56 is used to assist in maintaining the flap 24 in position after it is wrapped around the edge of the crotch portion of the panty as described below. The flaps 24 can be maintained in position by attaching the flaps 24 to the undergarment, or to the opposing flap. Suitable adhesive fasteners are described in greater detail in U.S. Pat. No. 4,917,697.

The fasteners used with the present invention are not limited to adhesive attachment means. Any type of fastener used in the art can be used for such purpose. For example, the sanitary napkin 20 could be secured to the wearer's undergarment by the fastener described in U.S. Pat. No. 4,946,527 entitled "Pressure-Sensitive Adhesive Fastener and Method of Making the Same" issued to Battrell on Aug. 7, 1990. For simplicity, however, the fasteners will be described in terms of adhesive attachment means.

The adhesive attachment means are respectively covered by removable release liners, central pad release liner and flap release liner, both designated 58. The pressure-sensitive adhesives should be covered with release liners 58 to keep the adhesives from sticking to extraneous surfaces prior to use. Suitable release liners are described in U.S. Pat. No. 4,917,697.

While a preferred sanitary napkin embodiment of the present invention has been described, numerous other sanitary napkin embodiments having flaps are available and are disclosed in the literature. These could be provided with the zones of differential extensibility of the present invention. In particular, sanitary napkins having flaps are disclosed in U.S. patent application Ser. No. 07/707,233 entitled "Sanitary Napkin Having Laterally Extensible Means for Attachment to the Undergarment of the Wearer", filed May 21, 1991 in the name of Osborn, et al., U.S. Pat. Nos. 5,009,653 and 4,950,264, both entitled "Thin, Flexible Sanitary Napkin" which issued to Osborn on Apr. 23, 1991 and Aug. 21, 1990, respectively, U.S. Pat. No. 4,917,697 entitled "Sanitary Napkin Having Flaps and Stress Relief Means" which issued to Osborn, III, et al. on Apr. 17, 1990, U.S. Pat. No. 4,687,478, entitled "Shaped Sanitary Napkin With Flaps", which issued to Van Tilburg on Aug. 18, 1987, U.S. Pat. No. 4,589,876, entitled "Sanitary Napkin", which issued to Van Tilburg on May 20, 1986, U.S. Pat. No. 4,285,343, entitled "Sanitary Napkin", which issued to McNair on Aug. 25, 1981, U.S. Pat. No. 3,397,697, entitled "Disposable Sanitary Shield For Undergarments", which issued to Rickard on Aug. 20, 1968, and U.S. Pat. No. 2,787,241, entitled "Sanitary Napkin", which issued to Clark on Apr. 2, 1957.

Suitable absorbent articles in the form of pantiliners are disclosed in U.S. Pat. No. 4,738,676 entitled "Pantiliner" issued to Osborn on Apr. 19, 1988. Suitable absorbent articles, at least some of which are in the form of adult incontinence products, are described in U.S. patent application Ser. No. 07/637,571 entitled "Absorbent Article Having Rapid Acquiring Wrapped Multiple Layer Absorbent Body" filed by Barry R. Feist, et al. on Jan. 3, 1991.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

The characteristics of the flaps 24 will now be looked at in greater detail. The general construction of flaps 24 suitable for use in the present invention (without the zones of differential extensibility) is described in greater detail in the patents incorporated by reference herein.

The overall size of the flaps 24 can be readily selected by those skilled in the art. Preferably, the flaps 24 are sized so that the sanitary napkin 20 is from about 10 to about 23 centimeters wide between the distal edges 34 of the flaps at their greatest separation. Preferably each flap 24 is from about 5 to at least about 19 centimeters long in the direction parallel to the principal longitudinal centerline 1 of the sanitary napkin.

The shape of the flaps 24 can be selected by those skilled in the art. Preferably, not only are the flaps 24 mirror images of each other, the two halves of each flap 26 and 28 are also symmetrical about the flap transverse centerline $t_1$. (It should be understood that the shape and orientation of the flaps described herein are those of a preferred embodiment. They are not mandatory design features.)

In the preferred embodiment illustrated in FIG. 1, the flaps 24 are positioned slightly forward of the principal transverse centerline t of the sanitary napkin. (In such a case, the flap transverse centerline $t_1$ does not coincide with the principal transverse centerline t of the sanitary napkin 20.) The flaps 24, however, are preferably evenly spaced from the principal longitudinal centerline 1 of the sanitary napkin.

The flaps 24 can be associated with the main body portion 22 in a number of different manners. Many of the different ways a component (such as the flaps 24) can be "joined to" or "associated with", etc. another component which are set forth in the definitions of these terms contained in U.S. Pat. No. 5,007,906 entitled "Decoupled Sanitary Napkin" which issued to Osborn, et al. on Apr. 16, 1991. When the flaps comprise separate elements, they can be joined to the main body portion 22 by any techniques known to those skilled in the art. Such techniques include, but are not limited to adhesives, heat and/or pressure, ultrasonics, etc.

The flaps 24 are associated with the main body portion 22 along lines of juncture 30. The lines of juncture can be concave, straight, (or, but preferably not convex) relative to the principal longitudinal centerline 1. The lines of juncture 30 may comprise those lines or areas where separate flap elements are joined to the main body portion 24. Alternatively, when the flaps 24 are integral with the main body portion 22, the lines of juncture 30 may represent lines of demarcation between the main body portion 22 and the flaps 24 (although it is not necessary that there be a precise line of demarcation).

It is also not necessary that the flaps 24 extend from (or be joined along) the longitudinal edges 22a of the main body portion 22. The flaps 24 can joined inward (or "inboard") from the longitudinal edges 22a toward the longitudinal centerline. The flaps 24 can, thus, each be joined to the main body portion 22 along the principal longitudinal centerline 1, or along the longitudinal edges 22a of the main body portion 22, or at any place between the principal longitudinal centerline 1 and the longitudinal edges 22a of the main body portion 22. The flaps 24 will, of course, generally be on opposite sides of the principal longitudinal centerline 1.

Having now described some sanitary napkins that can be used in conjunction with the present invention (as well as the characteristics of their flaps), the sanitary napkin of the present invention will now be described in greater detail with relation to the function of the same in the wearer's undergarments.

Figure 3:
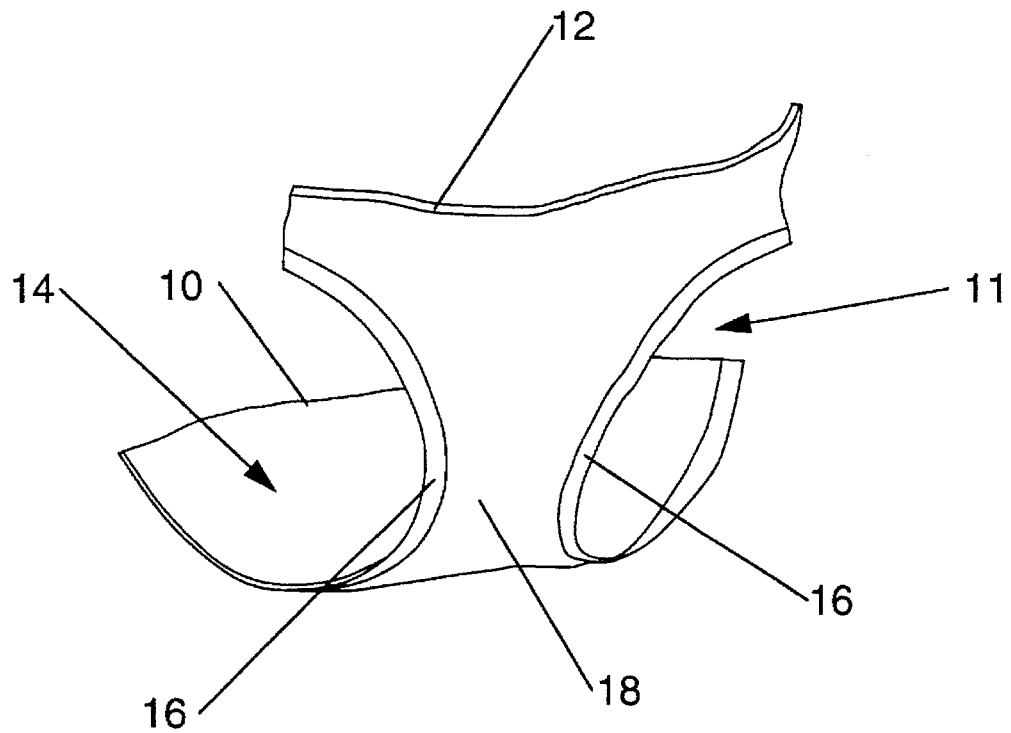
FIG. 3 is a perspective view of the crotch portion of a women's panties.

FIG. 3 is a depiction of the crotch portion 14 of an undergarment 11 of the type commonly worn by many women and well known as a panty. A panty 11 comprises a front section 10, a back section 12, and a crotch portion 14 which Joins the front and back sections. The crotch portion 14 comprises two side edges 16 and center crotch portion 18.

Figure 4:
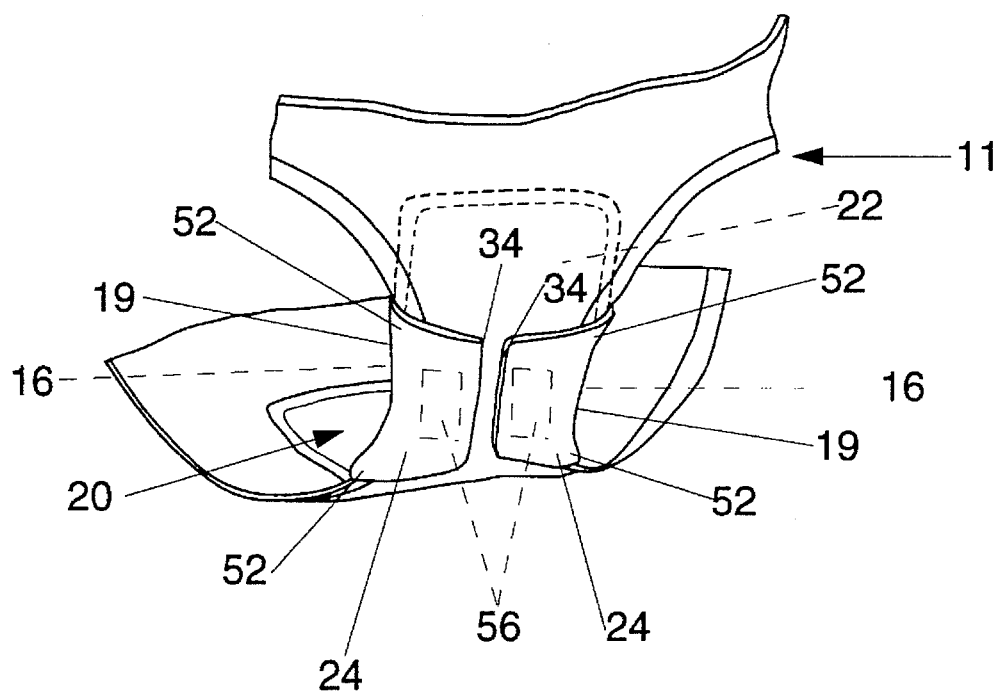
FIG. 4 is the same perspective view of the women's panties shown in FIG. 3 with the sanitary napkin embodiment of FIG. 1 being placed therein for use.

The sanitary napkin 20 of the present invention is utilized by removing the release liners 58 and placing the sanitary napkin 20 in a panty 11 as shown in FIG. 4. The center of main body portion 22 is placed In crotch portion 14 of the panty with one end of main body portion 22 extending towards the front section 10 of the panty and the other end towards the back section 12. The backsheet 42 is placed in contact with the inner surface of center crotch portion 18 of the panty. Central pad adhesive 54 maintains main body portion 22 in position. The distal portions of flaps 24 are folded around the side edges 16 of the panty. The flap adhesives secure the flaps 24 to the underside of the panty.

When the flaps 24 are folded down around the edge 16 of the crotch portion 14 of the panty, stresses are developed in the flaps, particularly in the corner regions 52' of the same. These stresses are magnified when the flaps 24 are folded under the panty and attached to the panty's underside. The stresses are further magnified when the panty is pulled up into position and the elastics in the panty edges 16 force the folded portion of the flaps into the uppermost part of the wearer's crotch and thigh.

The stresses are most highly concentrated along the fold 19 where the flap 24 changes from being disposed on the bodyside of the panty to being located on the underside of the panty. In other words, the stresses are concentrated at the edge 16 of the crotch portion 14 of the panty 11. The stresses in the flaps 24 generally follow the arc formed by the edges 16 of the crotch portion 14. These stresses may cause the corner regions 52' of the flaps 24 to bunch longitudinally inward. This reduces the area of the wearer's undergarments the flaps are able to cover. If the stresses are great enough, the flaps 24 can become detached from the panty and the flaps 24 will be less than optimally effective. Depending on the design of the sanitary napkin, the arc of concentrated stresses may or may not coincide with the lines of juncture 30 between the flaps 24 and the main body portion 22.

In order to eliminate, or at least reduce these stresses, the sanitary napkin 20 is provided with zones of differential extensibility 50. The zones of differential extensibility 50 preferably reduce the stresses along the fold 19 to such a degree that the flaps 24 will remain attached to the underside of the panty and will not lose their ability to cover a given area of the wearer's undergarments.

Referring again to FIG. 1, one preferred type of zone of differential extensibility 50 which was described briefly above, comprises the slack in the corner regions 52' of the flaps. The characteristics of the zones of differential extensibility 50 are described in greater detail below. That is followed by a discussion of some alternatively preferred types of zones of differential extensibility.

The zones of differential extensibility 50 are, as noted above, most preferably located at those points where the edges 35 of the flaps 24 intersect the edges 16 of the panty when the sanitary napkin 20 is worn.

The points of intersection can generally be determined by having a person wear a particularly designed napkin having flaps and a fairly commonly designed panty. Commonly, panties have a crotch width of about 5.0 to about 9.0 centimeters. Marks can then be made on the bottom surface of the sanitary napkin 20 where the sanitary napkin 20 intersects the panty. The points of intersection between the flap 24 and the edge 16 of the panty generally coincide with the ends of the fold 19. Assuming the napkin has two flaps, the four marks will mark the general locations for the zones of differential extensibility 50. The zones of differential extensibility 50 may be located along the lines of juncture 30, outboard of the lines of juncture in the flaps 24, or inboard of the lines of juncture. Commonly, the zones of differential extensibility 50 will begin at a point located between the area of the flap transverse centerline $t_1$ and about 1.5 centimeters in the longitudinal direction from the flap transverse centerline $t_1$.

The zones of differential extensibility 50 may be of any shape. Typically, they will form a three-sided figure (roughly triangular, pie-shaped, or fan-shaped) in plan view when they are fully extended. Often, the figure defined by the zones of differential extensibility will have two sides that are of approximately equal length and a shorter side. The edge 35 of the flaps 24 usually forms the shorter side. It should be understood, however, that the precise shape of the zones of differential extensibility 50 is not always as critical as the location and extensibility properties of the same. Likewise, it is not critical for there to be precise line of demarcation that marks the boundaries of the zones of differential extensibility 50 (or the boundaries of the complementary first portions of the quarters of the sanitary napkin). Thus, there can be a gradual transition between the zones of differential extensibility 50 and the first portions of the quarters of the sanitary napkin.

The zones of differential extensibility 50 may be bounded on one side by the line of juncture 30. Alternatively, the boundary may be adjacent the line of juncture 30. If the zones of differential extensibility 50 are provided in the main body portion 22 (for instance, if they are formed by a fold made through the main body portion 22 (as described below)), however, this boundary may be as far inboard as the principal longitudinal centerline 1. The zones of differential extensibility 50 are typically bounded at the ends by at least a portion of the edge 35 of the flap 24. This is often a curved line. (The zones of differential extensibility 50 can also be bounded at the ends by a portion of the longitudinal edges 22a of the main body portion and/or transverse or end edges 22b of the main body portion 22.) The third side of the zones of differential extensibility is typically formed by a boundary 51 which may be an imaginary line that runs from the point of the zone of differential extensibility 50 which is either located on the flap transverse centerline $t_1$ (or nearest to the same), to a point on the edge 35 of the flap 24.

The total area covered by the zones of differential extensibility 50 can vary widely. The area can cover a relatively large portion of the sanitary napkin, provided there remain some portions of the sanitary napkin adjacent at least portions of the principal longitudinal centerline and the flap transverse centerline that are less extensible. The zones of differential extensibility 50 can be provided along the entire juncture 30 of the flaps 24 with the main body portion 22. In alternative embodiments, the zones of differential extensibility 50 can be provided throughout the entire flap (for instance, if the entire flap is pleated with longitudinally-oriented pleats). Preferably, however, in the present invention, zones of differential extensibility 50 are not provided either along the entire juncture 30 or throughout the entire flap. There are several reasons for this.

First, due to the curvature of the panty crotch, all portions of the flaps are not stressed the same amount when the flaps are wrapped around a panty crotch. Typically, the portion of the flaps located adjacent the flap transverse centerline $t_1$ (the center portion 27 of the flap) will not be subjected to stresses that are as great as those exerted on the flap corner regions 52'. Thus, it is possible that the center portion 27 of the flaps (and possibly also the adjacent regions of the main body portion 22) could be constructed so that it is not provided with any extensibility properties. Alternatively, the center portion 27 (and adjacent regions) could merely be less extensible than the corner regions 52 of the sanitary napkin.

Second, it is preferable that the corner regions 52' of the flaps 24 stretch a greater distance in the transverse direction than the center portion 27 of the flaps for the best fit and for the flaps 24 to adapt properly to the curvature of the crotch of the wearer's undergarments. This allows the boundary 51 defined by the zones of differential extensibility to correspond to the configuration of the edges of the crotch of the wearer's panties.

Third, depending on the process used to create the zones of differential extensibility 50, it may be less expensive to provide differential extensibility in only certain portions of the sanitary napkins.

The amount of differential extensibility needed can vary depending on a number of factors. These include, but are not limited to the size and configuration of the wearer's panties, the size and configuration of the flaps, etc. Any amount of differential extensibility in the corner regions 52 will provide some benefit versus a sanitary napkin that is not provided with zones of differential extensibility. The amount of differential extensibility should not be so great, however, that the excess material that comprises the zones of differential extensibility 50 causes the sanitary napkin to fit sloppily adjacent the wearer's panties and her body.

Preferably, the amount of differential extensibility is sufficient to substantially reduce the stresses on the flaps when the sanitary napkin is worn. Typically, a conservatively configured zone of differential extensibility 50 is one which when fully extended, defines a linear boundary 51 (i.e., one which forms a straight line) that runs from the intersection of the flap transverse centerline $t_1$ and the line of juncture 30 to the point on the edge 35 of the flap 24 where the flap 24 intersects the edge 16 of the panty crotch. A zone of differential extensibility 50 with a linear configuration is said to be conservatively configured because it will ordinarily provide a sufficient amount of extensibility in most cases to relieve the stresses in the flaps 24. In an ideal case, the boundary 51 will correspond to the configuration of the edges 16 of the crotch of the wearer's panties.

Figure 2:
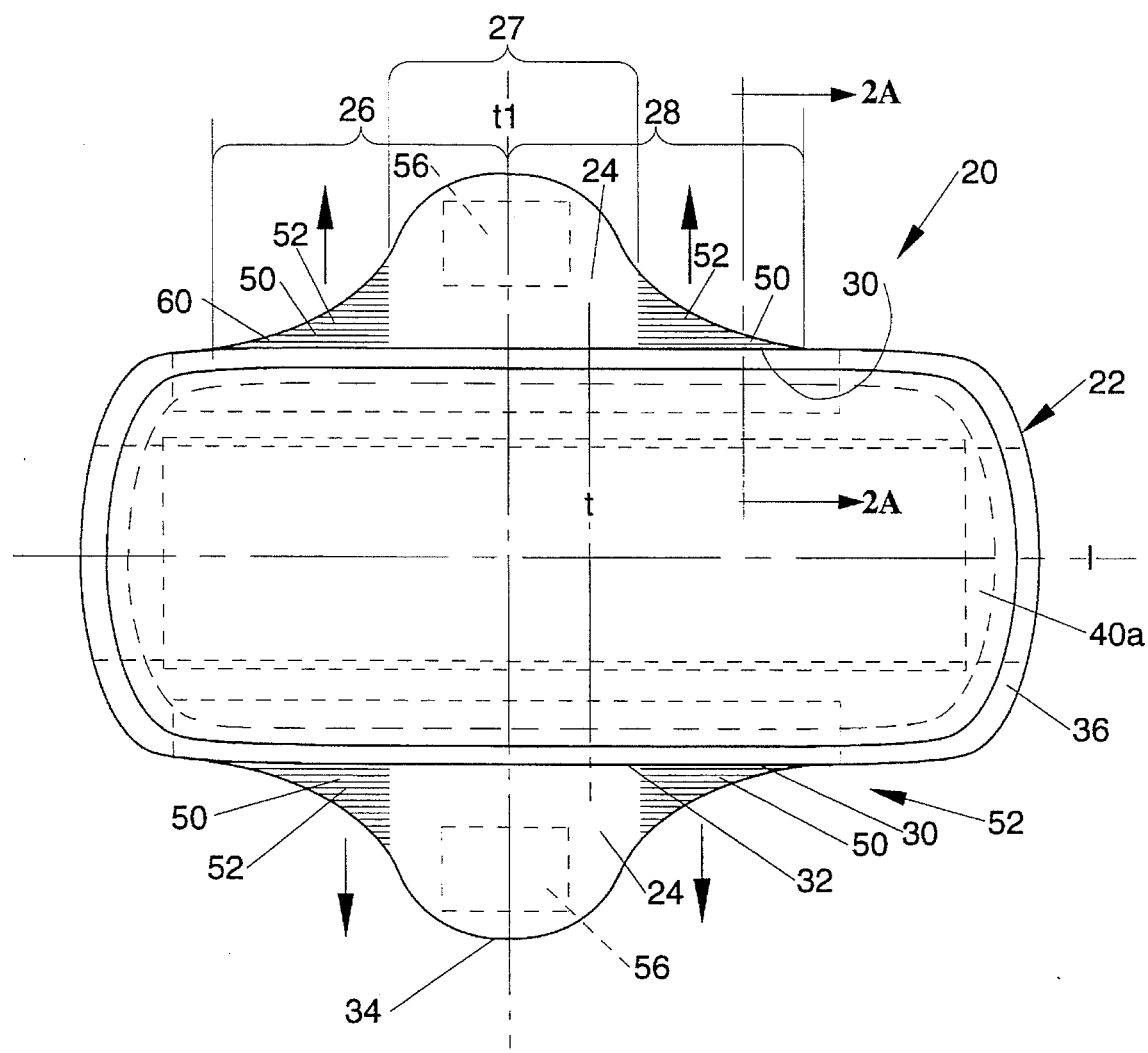
FIG. 2 is a top plan view of a sanitary napkin embodiment of the present invention having flaps with an alternatively preferred type of zones of differential extensibility.
Figure 2A:
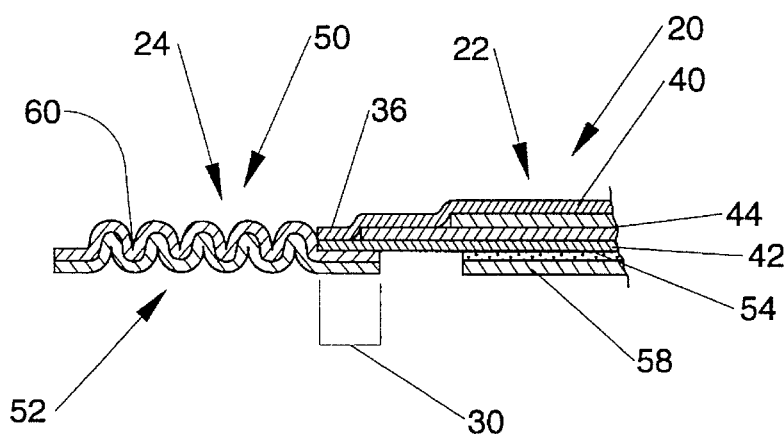
FIG. 2A is a lateral cross-sectional view taken along line 2A—2A of FIG. 2 through one of the flaps of the sanitary napkin.

FIGS. 2 and 2A show a sanitary napkin having another type of zone of differential extensibility. The sanitary napkin 20 shown in FIGS. 2 and 2A has flaps with corner regions 52 that have been provided with differential extensibility by ring rolling these corner regions in accordance with the above-described ring rolling patents and patent applications. The ring rolling (or pre-corrugating) should be applied so that the fold lines 60 in the corrugations are oriented generally in the longitudinal direction. The phrase "generally in the longitudinal direction" (and similar phrases), as used herein, means oriented more in the longitudinal direction than in the transverse direction. Thus, the fold lines 60 may angle away from the principal longitudinal centerline 1. This will also provide the desired transverse direction extensibility.

In variations of the embodiments of the present invention (such as the embodiment shown in FIGS. 2 and 2A, the amount of extensibility provided can be varied throughout different portions of the zones of differential extensibility 50. For instance, the number or amplitude of the corrugations formed by the ring rolling could be varied so that either or both these characteristics are greater further from the flap transverse centerline $t_1$. This will allow the sanitary napkin to be provided with differential extensibility characteristics that most closely match the configuration of a panty crotch.

Figure 5:
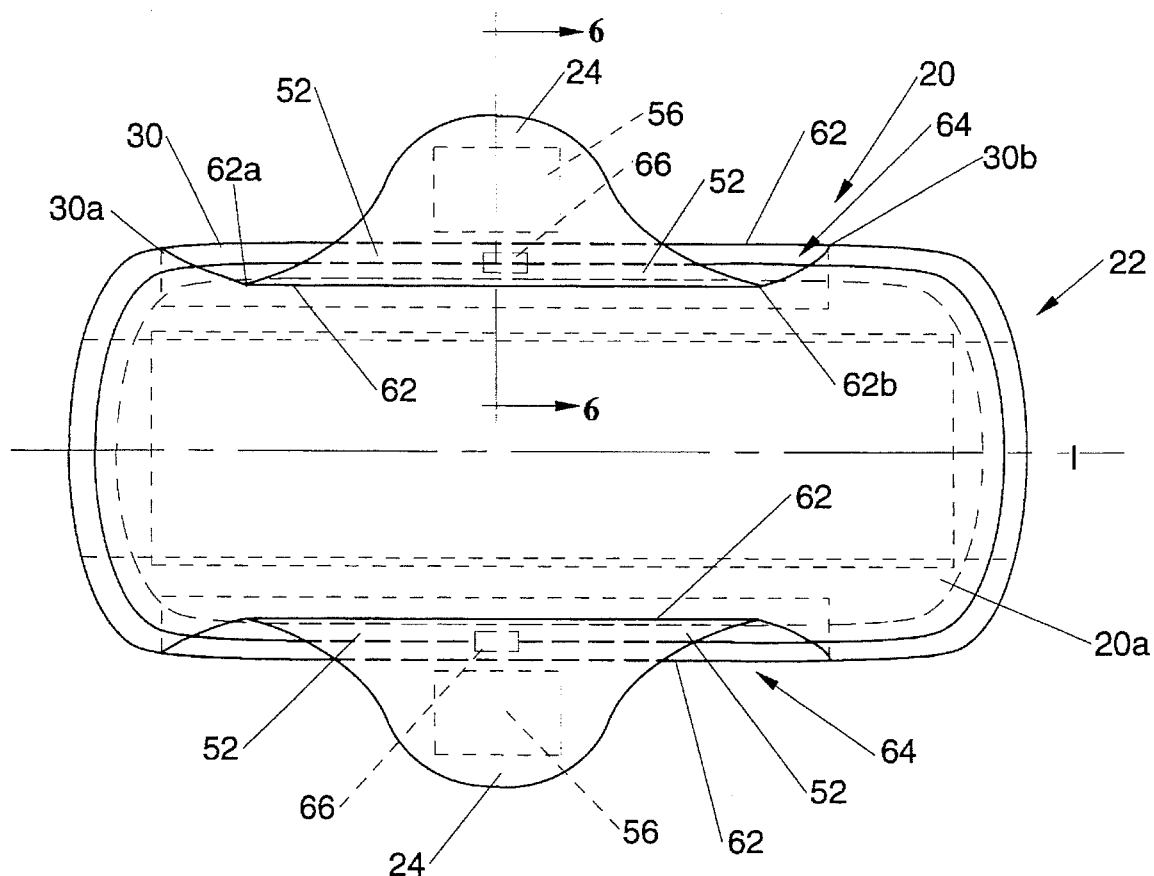
FIG. 5 is a top plan view of an alternatively preferred sanitary napkin embodiment of the present invention.
Figure 6:
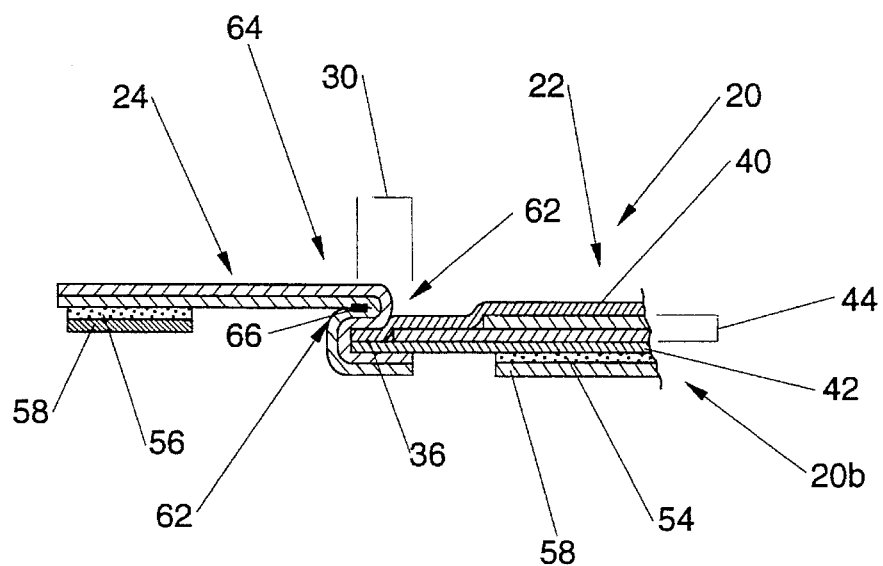
FIG. 6 is a cross-sectional view of the sanitary napkin embodiment shown in FIG. 5 taken along line 6—6 of FIG. 5.

FIGS. 5 and 6 show another alternative embodiment of the sanitary napkin of the present invention. The sanitary napkin 20 shown in FIGS. 5 and 6 has been provided with zones of differential extensibility 50 by pleating and then gathering in portions of the flaps.

The flaps 24 are pleated or folded with generally longitudinally-oriented fold lines 62. The fold lines 62 can run along and/or outboard (or even inboard) of the juncture 30 of the flaps and the main body portion 22. The pleats preferably run the length of the juncture 30. The pleated sections of the flaps (the "pleats") 64 are preferably folded on top of each other (that is, stacked perpendicular to the plane of the sanitary napkin). In alternative embodiments, they may be folded and arranged side-by-side. The pleated sections are gathered in or restrained from opening by a flap pleat restraint 66 located along the flap transverse centerline t1. This provides the sanitary napkin, and particularly the flaps 24, with corner regions which are extensible in the transverse direction and with center portions 27 (along the flap transverse centerline $t_1$) which are not.

In such a pleated embodiment, the flaps 24 can be provided with any number of fold lines. For instance, in the most basic form of the pleated embodiment, the flaps can simply be folded inward toward the principal longitudinal centerline 1 along a single line along the juncture 30 and tacked to the main body portion 22 at a point inboard of the juncture 30 (which is preferably in the area of the flap transverse centerline $t_1$). Typically, however, as shown in FIG. 6, the flaps will have at least two pleat fold lines 62.

The flap pleat restraint 66 can be any suitable type of element capable of keeping a portion of the pleated material from unfolding. The flap pleat restraint 66 can be located along the flap transverse centerline $t_1$, or it can be spaced some distance away from the flap transverse centerline $t_1$. The flap pleat restraint 66 is, however, preferably located at some place along the flap transverse centerline $t_1$. This creates flaps with pleats which are able to open up an equal amount in both the front and back halves 26 and 28 for a preferred fit around the panty crotch. The flaps 24 can have two flap pleat restraints 16, one located along (or spaced some distance away from) the flap transverse centerline $t_1$ for each flap, or they can have a single flap pleat restraint that spans from one flap to the other.

The flap pleat restraint 66 shown in FIG. 6 is an "interior" restraint, i.e., it is located in between two pleated or folded sections 64 of the flaps 24. In alternative embodiments, the flap pleat restraint 66 can be of a type which secures the pleated sections 64 of the flaps 24 from outside (or exterior) of the pleated sections.

The flap pleat restraint 66 may be of any size provided it is no larger than the length of the juncture 30. This allows the pleated sections 64 of the flaps 24 to open properly. This is the case since the pleated sections 64 of the flaps 24 will typically open from the ends 30a and 30b of the lines of juncture to the flap pleat restraint 66. It may, therefore, be preferable for the flap pleat restraint 66 to be as small as possible to minimize interference with the opening of the pleated sections 64. The flap pleat restraint 66 should also be located at a point on the pleated section 64 that is relatively close to the principal longitudinal centerline 1. This will ensure that the pleat will not unfold and lose its effectiveness.

The flap pleat restraint 66 can be of any suitable construction. Suitable flap pleat restraints 66 include, but are not limited to adhesives, ultrasonic bonds, heat and/or pressure bonds, tapes, etc. These different types of flap pleat restraints can be in an unlimited number of configurations. Such configurations can include spots, lines, patches, etc.

The dimensions of some suitable pleats for embodiments such as those shown in FIGS. 5 and 6 are set forth in the following Table 1:

TABLE 1

| PLEAT SIZES | | |
|---|---|---|
| Length of Flap (in.) | Width of Pleat (in.) | Effective Pleat Size (in.) |
| 3 | 0.43 | 0.14 |
| 3.5 | 0.50 | 0.19 |
| 4 | 0.58 | 0.26 |
| 4.5 | 0.65 | 0.33 |
| 5 | 0.73 | 0.40 |

TABLE 1-continued

| PLEAT SIZES | | |
|---|---|---|
| Length of Flap (in.) | Width of Pleat (in.) | Effective Pleat Size (in.) |
| 5.5 | 0.81 | 0.50 |
| 6 | 0.90 | 0.60 |
| 6.5 | 1.00 | 0.72 |
| 7 | 1.11 | 0.86 |
| 7.5 | 1.23 | 1.03 |
| 8 | 1.40 | 1.24 |

The dimensions in Table 1 are non-limiting examples of the sizes of pleats which may be useful in providing a sanitary napkin with suitable zones of differential extensibility 50. The dimensions are based on a sanitary napkin embodiment which has a pleat 9 inches long. The length of the pleat (designated $P_1$ in FIG. 15) is measured from one end of the line of juncture to the other (from 30a to 30b) in a direction parallel to the principal longitudinal centerline 1.

The length of the flaps 24 referred to in Table 1 is measured along the pleat line 62 that is closest to the distal edge 34 of the flap 24 when the pleat restraint 66 is removed and the flap is unfolded. The distance between these two points 62a and 62b is designated $F_1$ in FIG. 15. The width of the pleat, $P_w$, is the distance between fold lines 62. The "effective pleat size" refers to a number calculated by multiplying the width of the pleat times the ratio defined by the length of the flap over the length of the pleat.

Figure 15:
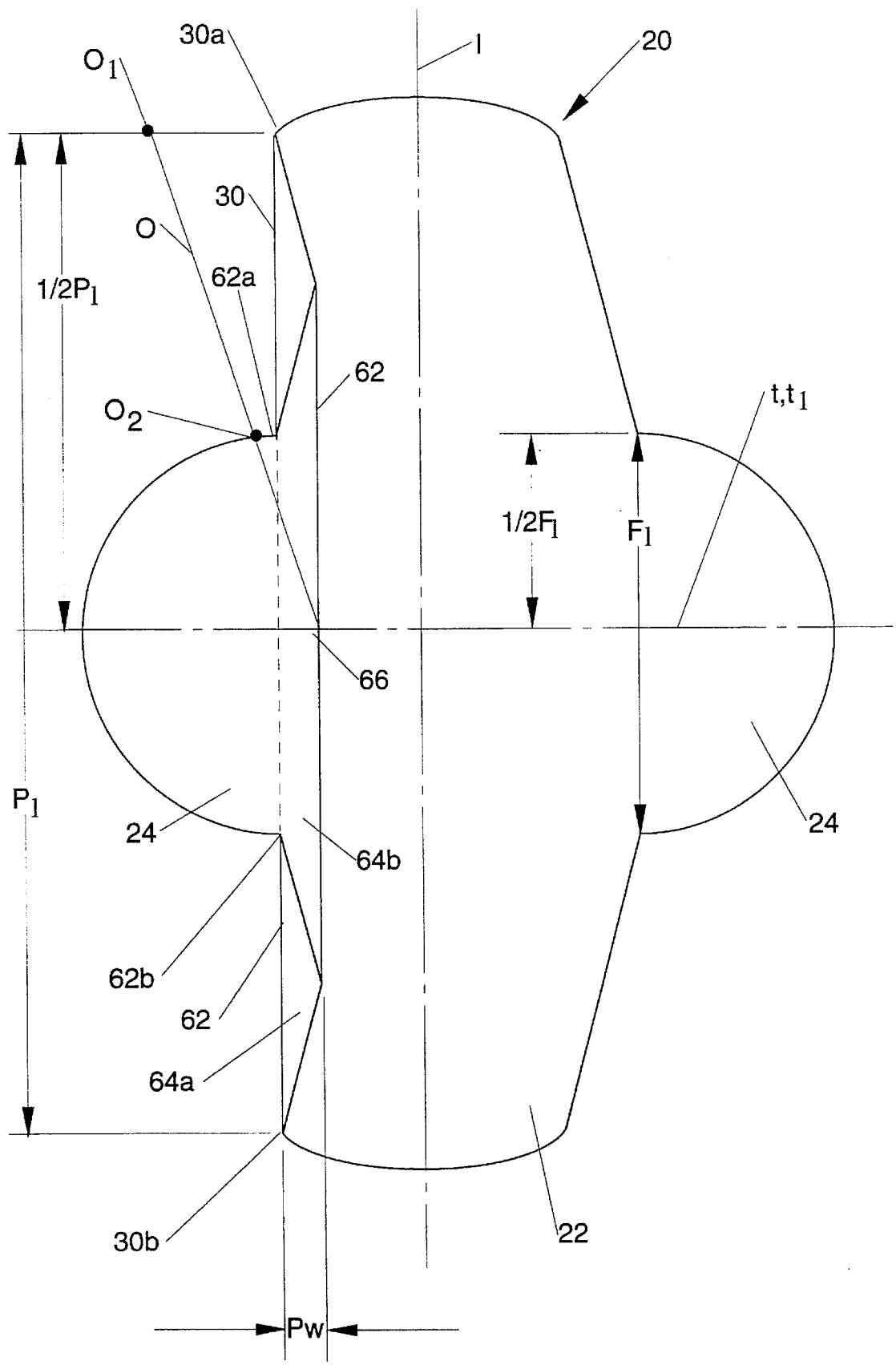
FIG. 15 is a diagram which illustrates some of the terms and concepts described in Table 1.

The effective pleat size serves as an approximation of the amount the pleat will open in the corner regions 52 of the sanitary napkin. FIG. 15 shows this schematically. The line designated 0 in FIG. 15 represents the approximate location of edges of the pleated sections when the pleat is in a fully opened or extended configuration. FIG. 15 shows that in this embodiment the points on the pleated sections spaced longitudinally farthest from the flap transverse centerline $t_1$ will generally fan open fully (toward to point $0_1$) while the points such as 62a in the corner regions 52 of the sanitary napkin will only open partially (to point $0_2$). The effective pleat size recognizes that the lesser amount which the pleated sections will open in the corner regions is directly proportional to the relationship between the length of the flaps and the length of the pleat (i.e., perhaps better understood and more specifically as being proportional to the ratio defined by ½ $F_1$ over ½ $P_1$).

The width of the pleat and the number of folds in the pleats determines the amount of extensibility of the pleated material. The amount of extensibility (or slack material) in the corner regions 52 can, thus, be calculated by multiplying the number of folded sections of the pleated section times the effective pleat size. Thus, in embodiments shown in FIG. 15 having two folded sections 64a and 64b, the amount of slack in each corner region 52 is approximately equal to twice the effective pleat size.

In addition to being useful for determining the amount of extensibility in the corner regions of pleated sanitary napkin embodiments, the effective pleat size and other measurements provided herein can even be used more broadly. The effective pleat size figures provided can be used as guidelines for determining the amount of extensibility for the embodiments described herein having different types of zones of differential extensibility. The relationship between the dimensions of the pleats provided above and the dimensions of interest in the other embodiments described herein can be arrived at by one skilled in the art. (For example, FIG.

15 shows an example of the use of pleat widths. The curved dotted line shown in FIG. 15 represents a suitable location for the curved juncture in the embodiment (described below) in which zones of differential extensibility 50 are provided by attaching the flaps 24 along a curved juncture. The curved juncture curves inward in an amount equal to the width of the pleat.)

Figure 7:
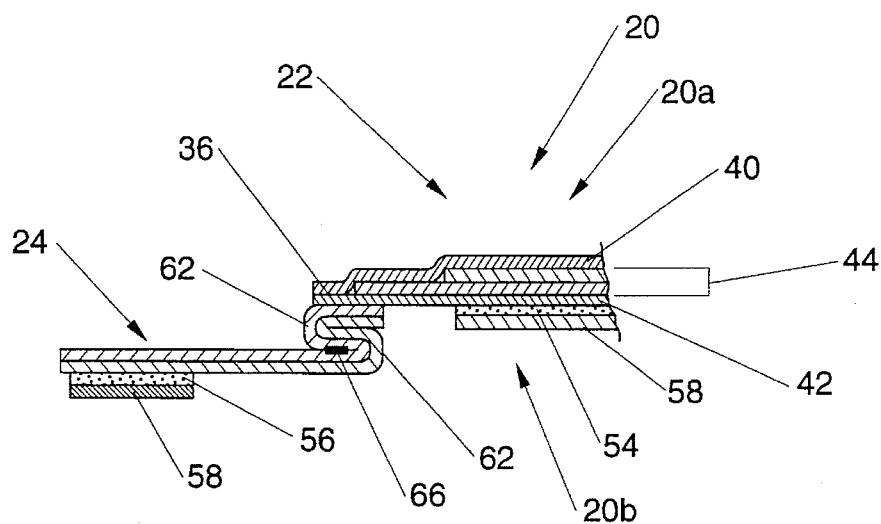
FIG. 7 is a cross-sectional view of another sanitary napkin embodiment taken from an angle similar to that of FIG. 6 having a pleat joined to its backsheet.

FIG. 7 shows an alternative embodiment of a sanitary napkin having pleated flaps in which the flaps 24 are pleated, folded over, and secured to the garment side 20b of the sanitary napkin 20 rather than the body-facing side 20a (as in the embodiment shown in FIG. 6).

Figure 8:
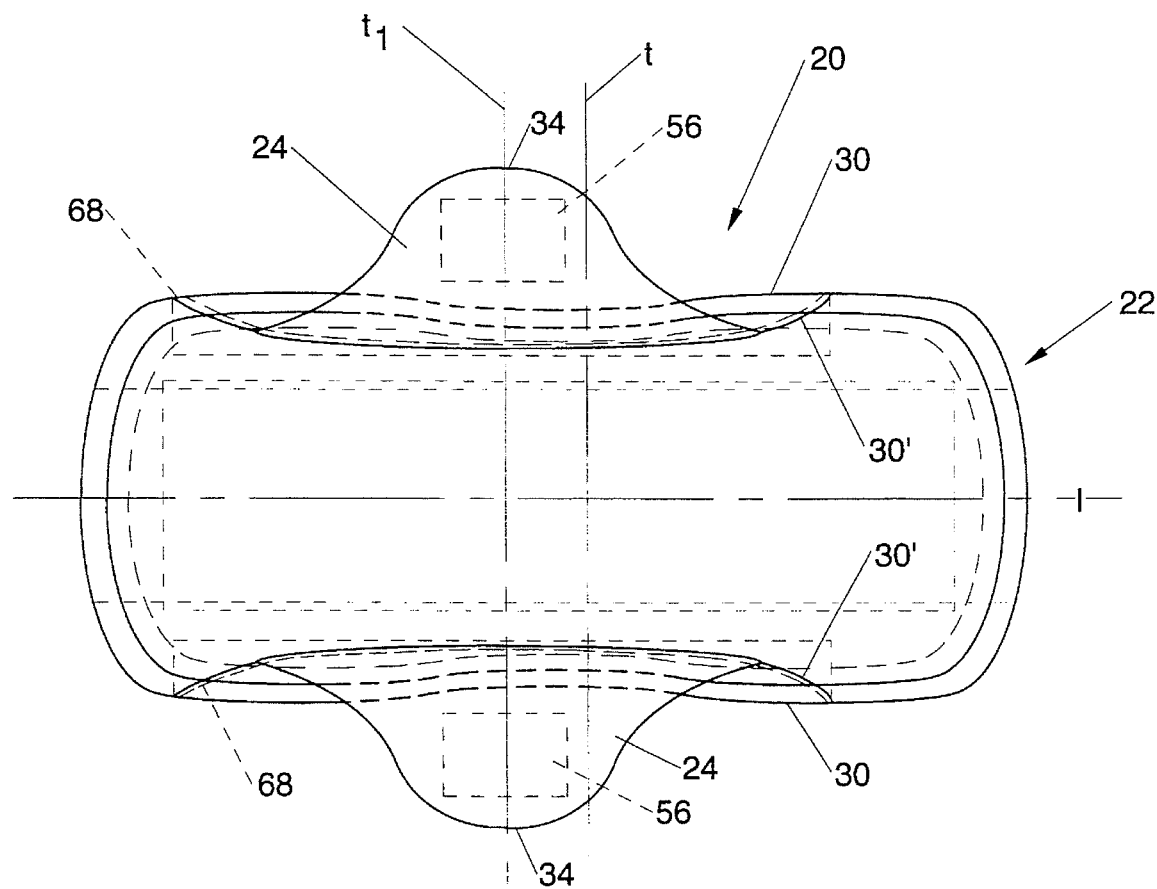
FIG. 8 is plan view of a sanitary napkin embodiment showing a curved pattern of joining the flap to the main body portion of the sanitary napkin.

FIG. 8 shows another alternative embodiment of the sanitary napkin 20 of the present invention in which the flaps 24 are attached along lines of juncture that are curved concave inward toward the principal longitudinal centerline 1. When the flaps 24 in such an embodiment are folded outward, excess flap material is present in the corner regions 52.

In this embodiment, the sanitary napkin 20 may have two longitudinal junctures, such as 30 and 30', adjacent each longitudinal edge of the main body portion.

The sanitary napkin 20 can have a first longitudinal juncture (or an "outboard" longitudinal juncture) 30 where the flap 24 is attached to or extends from the main body portion 22. A second longitudinal juncture can be present (or "inboard" longitudinal juncture) 30' that is used to provide the sanitary napkin 20 with the desired zones of differential extensibility 50.

The first longitudinal juncture 30 is shown as being a curved line in FIG. 8. However, it need not be curved. It can be in any form described above as being suitable for the lines of juncture. The second longitudinal juncture 30', however, will generally always be curved concave inward toward the principal longitudinal centerline 1.

The sanitary napkin 20 shown in FIG. 8 can be made from any sanitary napkin that is provided with flaps. A securement means, such as a line of adhesive 68 is laid down on either the body-facing side 20a or the garment side 20b of the sanitary napkin in the pattern desired for the second longitudinal juncture (or "curved juncture") 30'. The flaps 24 are then folded over onto the aforementioned side of the sanitary napkin and sealed by the securement means. The securement means can comprise any means known in the art for securing such materials together including, but not limited to heat and/or pressure sealing, ultrasonics, and, of course, adhesives.

In a preferred embodiment, the excess flap material between the first and second longitudinal junctures 30 and 30' can be trimmed to provide the sanitary napkin 20 with curved longitudinal side edges. The formation of the zones of differential extensibility in this manner allows location and curvature of the curved juncture 30' to be controlled. In a preferred embodiment, the curvature of the curved juncture 30' can be established to coincide with the curvature of the panty crotch.

Figure 8A:
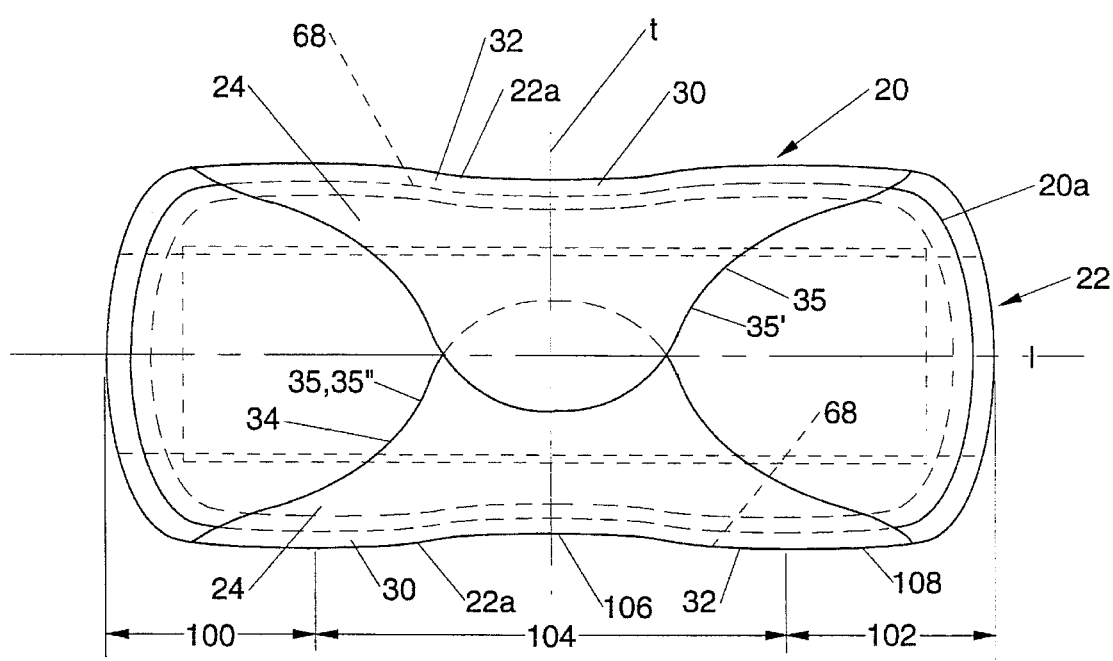
FIG. 8A is plan view of another sanitary napkin embodiment showing a curved pattern of Joining the flap to the main body portion of the sanitary napkin.

FIG. 8A shows an example of a sanitary napkin that employs another way of attaching the flaps 24 along a curved line of juncture 30.

In the embodiment shown in FIG. 8A, the flaps 24 are only attached along a single curved juncture 30. As shown in FIG. 8A, the longitudinal side edges 22a of the main body portion 22 are curved concave inward toward the principal longitudinal centerline 1. The flaps 24 are attached along the single juncture 30 that runs along the curvature of the longitudinal side edges 22a of the main body portion 22.

FIG. 8A also shows that the curved juncture 30 only needs to be curved concave inward in the central region 104 of the sanitary napkin. (The same is true for virtually all of the curved juncture embodiments described herein.) The curved juncture 30 can be in any suitable configuration in the end regions of the sanitary napkin. For instance, the juncture 30 can be straight, or (as shown in FIG. 8A) curved convex outward in the end regions 100 and 102. (The terms "central region" and "end regions" are defined in greater detail in U.S. Pat. No. 4,690,680 issued to Higgins on Sep. 1, 1987.)

In fact, the juncture 30 need not be curved at all to provide some of the desired benefits obtained when using a curved juncture. The juncture 30 only needs to have some points, such as 106, in the central region 104 of the sanitary napkin that are more inwardly disposed than the points, such as 108, that lie along the juncture 30 in the end regions 102 and 104 of the sanitary napkin. Thus, the juncture 30 could be formed by two or more straight lines or segments (and/or curved segments). The lines will typically be angled inwardly toward the principal longitudinal centerline 1 as they approach the central region 104 of the sanitary napkin. Curved Junctures are preferred, however, because they correspond most closely to the shape of the edges of the panty crotch.

The proximal edges 32 of the flaps 24 shown in FIG. 8A are either on, or slightly laterally outboard of the securement means 68. The proximal edges 32 of the flaps 24 can be of various different configurations as long as this relationship is maintained. Preferably, the curvature of the proximal edges 32 of the flaps 24 closely matches the curvature of the longitudinal side edges 22a of the main body portion 22.

The flaps 24 can be attached to either side (20a or 20b) of the sanitary napkin 20 (as in the case of many of the embodiments described herein). Preferably, however, the flaps 24 are attached to the body-facing side 20a of the sanitary napkin. This has the advantage that the sanitary napkin can be placed in the wearer's undergarments with the flaps 24 in the folded inward configuration shown in FIG. 8A. The user does not have to unfold, or otherwise manipulate the flaps 24 before attaching the main body portion 22 to the panty crotch. The flaps 24 are then folded back outward around the edges of the panty crotch and attached to the underside of the panty. Preferably, in cases such as this, where the flaps are initially oriented inwardly, they are comprised of a material sufficiently flexible that the flaps will not tend to fold back inward when they need to be folded back for attachment to the underside of the wearers panties.

FIG. 8A also provides an example of flaps 24 that can be manufactured with a minimum of wasted material. This is particularly important in cases where the flaps are made of a relatively expensive material.

Figure 8B:
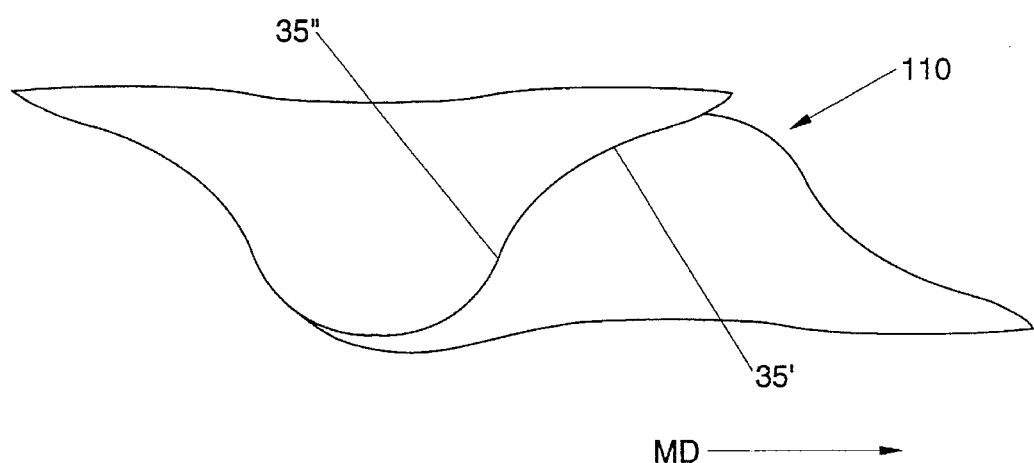
FIG. 8B is a plan view of a method of making flaps for the embodiment shown in FIG. 8A.

The flaps 24 for the embodiment shown in FIG. 8A are preferably cut prior to the attachment of the same to the main body portion 22. As shown in FIG. 8B, the flaps 24 are preferably both cut from the same web of material 110. The web of material 110 need only be as wide as the lateral width of one flap (or only slightly wider than the width of a flap). The edges of the web of material oriented in the machine direction can be trimmed to the desired curvature for the proximal edges of the flaps. After the edges are trimmed, the edges 35 of the flaps can be formed by cutting the web along a sinusoidal path.

The sinusoidal cutting path can have an amplitude that extends from one edge of the web to the other. The sinusoidal cutting path forms flap pieces which are "nested" with each other. The cutting path can, thus, simultaneously form the edges of two different flaps. For instance, the web of flap material can be cut so that the material forming the portion of the edges designated 35' and 35" is abutting and the sinusoidal cutting path forms both flap edges.

Figure 8C:
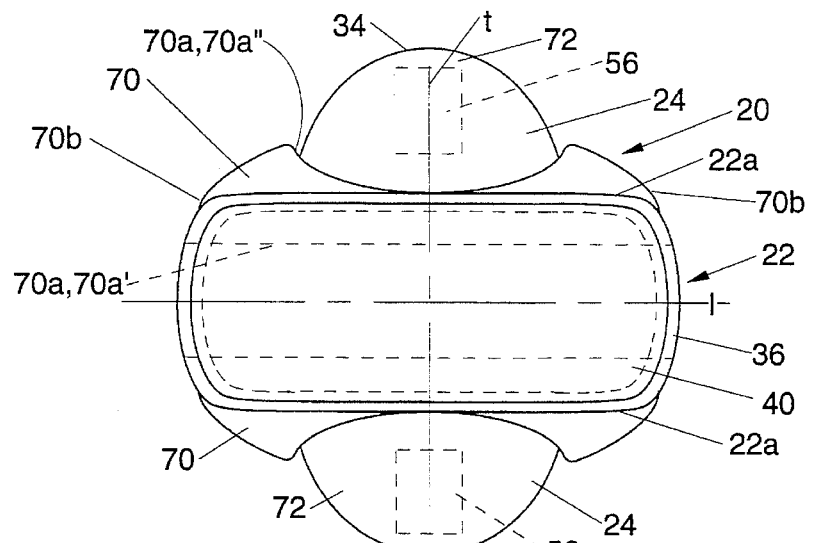
FIGS. 8C–8E are various top and bottom plan views of still another embodiment of a sanitary napkin in which the flaps are joined to the main body portion of the sanitary napkin along a curved juncture.
Figure 8D:
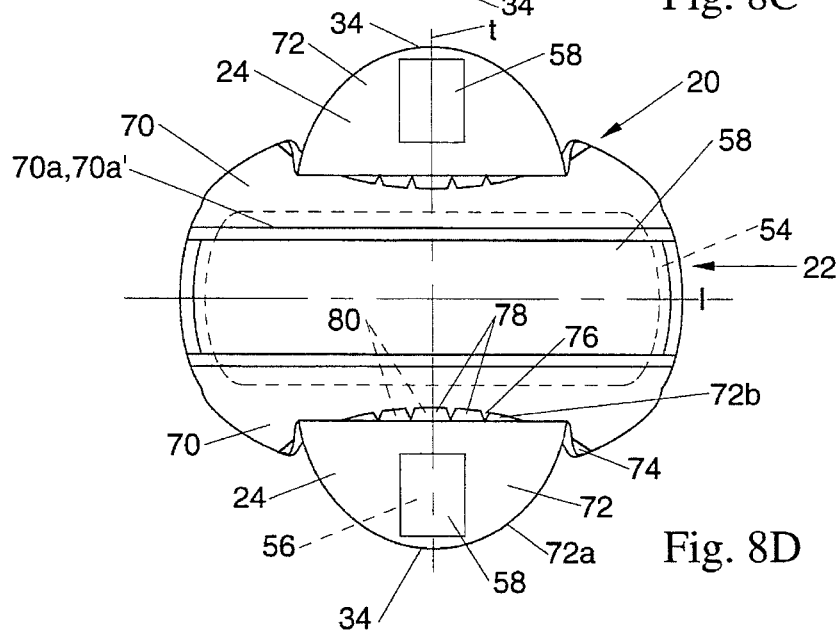
Figure 8E:
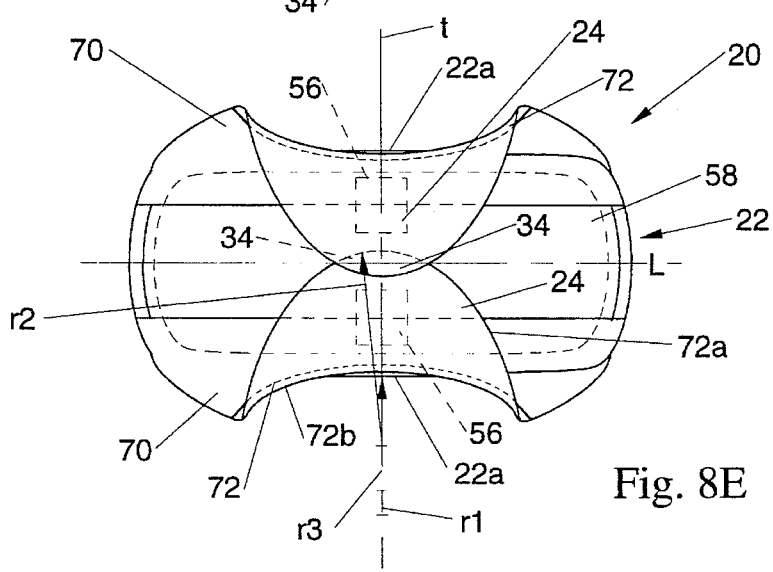

FIGS. 8C–8E show an example of a sanitary napkin that employs still another way of attaching the flaps 24 along curved lines of juncture 30 to create slack in the corner regions 52. The attachment is accomplished in the following manner.

In the embodiment shown in FIGS. 8C–8E, the sanitary napkin 20 flaps 24 that comprise separate pieces attached to the backsheet 42 (these pieces could, of course, be attached to another component of the sanitary napkin 20). The longitudinal side edges 22a of the main body portion 22 of the sanitary napkin 20, prior to the attachment of the flaps 24, are relatively straight.

A piece of material, extension 70, is provided which is attached along each longitudinal edge 22a of the main body portion 22. The extension 70 extends the longitudinal side edges 22a of the main body portion 22 of the sanitary napkin 20 outward from the direction of the principal longitudinal centerline 1. The extension 70 can be any suitable material. Preferably, the extension comprises backsheet material. In one preferred embodiment, the extension 70 comprises a nonwoven/fluid impervious film laminate similar to that described above as being suitable for use as the backsheet.

The extension 70 has two longitudinal edges 70a and two transverse edges 70b. The longitudinal edges 70a comprise a proximal longitudinal edge (or simply "proximal edge") 70a' and a distal longitudinal edge (or simply "distal edge") 70a". In the embodiment shown, the proximal edge 70a' of the extension 70 is preferably a relatively straight line and the distal edge 70a" is curved concave inward toward the principal longitudinal centerline 1 of the sanitary napkin. The radius of curvature of the distal edge 70a" is designated in FIG. 8E as the first radius of curvature, $r_1$.

The transverse edges 70b of the extension 70 can be of any suitable configuration. Preferably, the transverse edges 70b are of a curved convex outward configuration, similar to that shown in the drawings, so that they will present a comfortable shape for the wearer.

The flaps 24 are provided in the form of separate crescent-shaped pieces of material 72. The crescent-shaped pieces 72 each have two curved edges, 72a and 72b. One of the edges, 72a, has a smaller radius of curvature (second radius of curvature $r_2$) than the other edge 72b (which has a third radius of curvature $r_3$). The edges 72a with the smaller radius of curvature $r_2$ (i.e., the edge with more curvature) form the distal edge 34 of the flaps 24. The edges 72b with the larger radius of curvature $r_3$ form the proximal edges 32 of the flaps.

The radii of curvature are established so the third radius of curvature $r_3$, is less than the radius of curvature $r_1$ (the radius of curvature of the distal edge 70a" of the extension piece 70.)

There is a zone along the edge 72b with the larger radius of curvature that has a plurality of spaced apart notches 76 cut into it (shown in FIG. 8D). The zone comprises the flange 74 of the flaps 24. The flange 74 can be of any suitable dimensions which allows the flaps 24 to be attached to the extension 70. In the embodiment shown, the flange is about ¼ inch (about 0.6 mm.) in width. The notches 76 are preferably about 0.2 inch (about 0.5 mm.) in depth and about 0.15 inch (about 0.4 mm.) in width at their widest point. The notches 76 allow the flange 74 to spread out sufficiently so that the first and third radii of curvature, $r_1$ and $r_3$, become approximately the same. This allows the flaps 24 to be attached along the flange 74 to the edge of the extension piece 70 without puckering, etc.

The flange 74 can be attached to the extension 70 by any suitable securing element, or attachment means. For instance, as shown in FIG. 8D, the securing element used to attach the flaps 24 to the extension 70 can include, but is not limited to a plurality of spaced apart pieces of double-sided tape 80 that are placed along those areas of the flange 74, designated 7B, that lie between the notches 76. (The double-sided tape pieces are placed along the unnotched portions of the flange.)

In an alternative embodiment, which is somewhat preferred over the embodiment described above, the extension 70 can be made integral with the main body portion 22. That is, rather than attaching a separate extension piece to each longitudinal side edge of the sanitary napkin 20, the longitudinal side edges of the main body portion 22 (or a component thereof, such as backsheet 42) could merely be extended further outboard away from the principal longitudinal centerline 1. The longitudinal side edges 22a of the main body portion 22 could then be cut to form a curved edge similar to that of the distal edge 70a" of the extension 70 described above.

Figure 9:
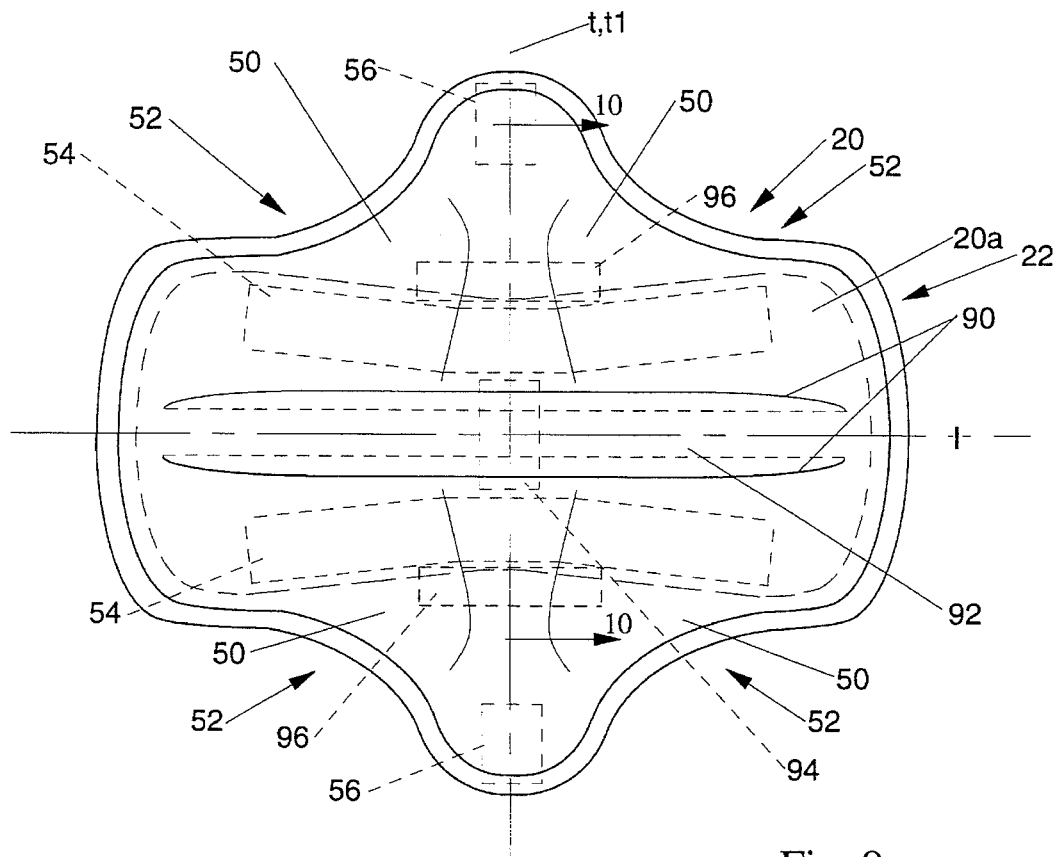
FIG. 9 is a top plan view of another embodiment of a sanitary napkin in which the main body portion of the sanitary napkin is folded.
Figure 11:
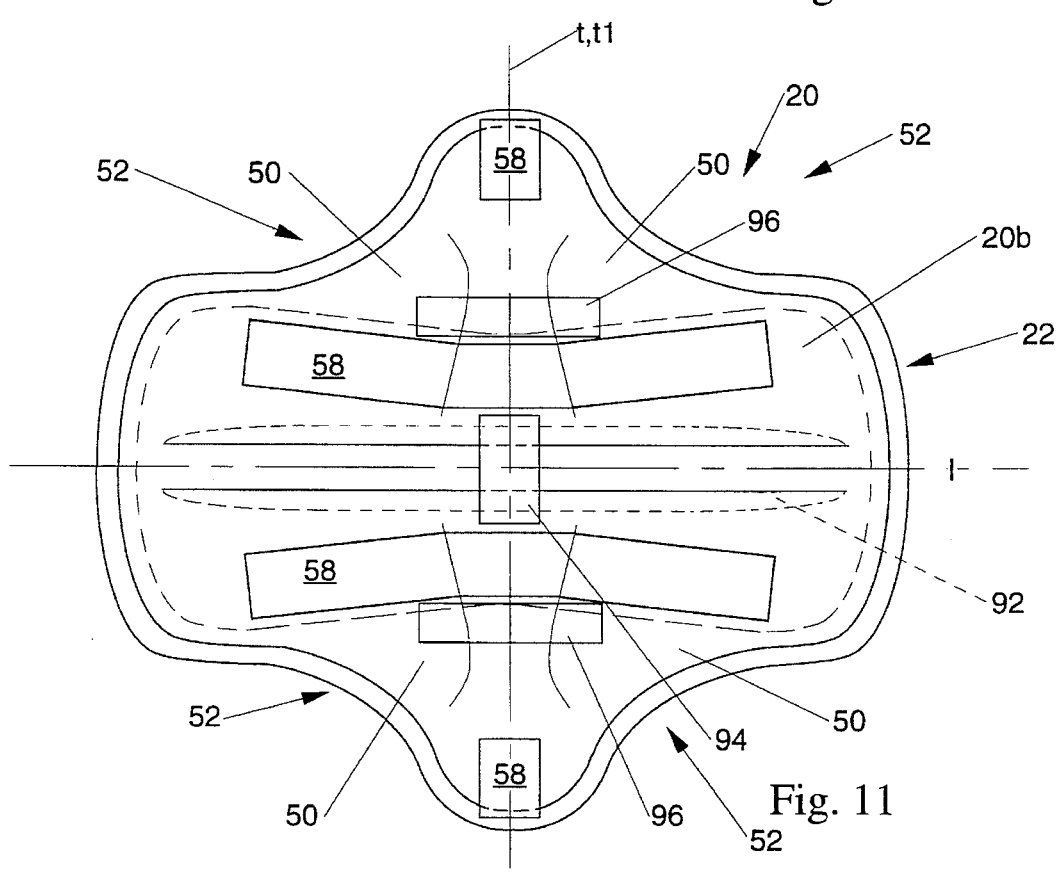
FIG. 11 is a bottom plan view of the sanitary napkin embodiment shown in FIG. 9.
Figure 10:
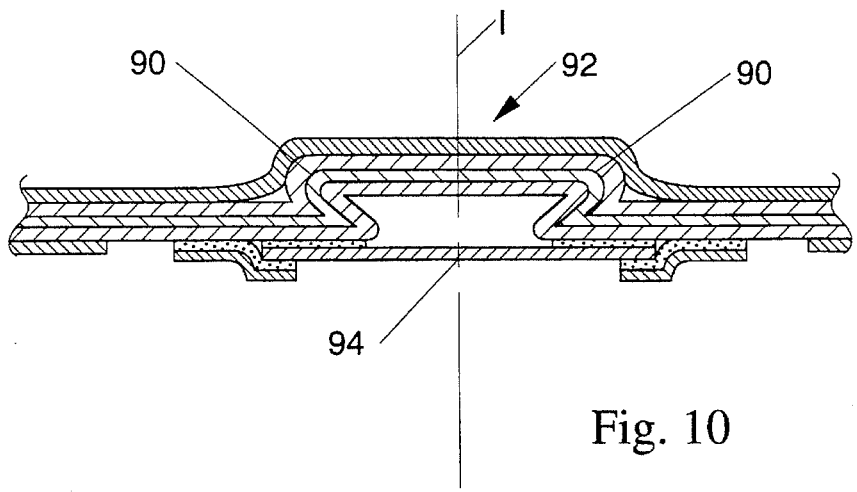
FIG. 10 is a simplified cross-sectional view of the sanitary napkin embodiment shown in FIG. 9 taken along line 10—10 of FIG. 9.

FIGS. 9–11 show still another alternative embodiment of the sanitary napkin 20 of the present invention. In this embodiment, the entire sanitary napkin 20 is folded or pleated through the main body portion 22 of the sanitary napkin. The sanitary napkin 20 is folded or pleated along two longitudinal lines 90, one of which is located on each side of the principal longitudinal centerline 1. The pleated section of the main body portion 22 is restrained from opening along the flap transverse centerline $t_1$.

This also creates zones of differential extensibility 50 (or slack) in the corner regions 52 of the sanitary napkin 20. The zones of differential extensibility 50 are formed in the flaps 24, as well as in portions of the main body portion 22, particularly those portions which lie between the corner regions of the flaps 52' and the principal longitudinal centerline 1. The zones of differential extensibility 50 are formed because the portions of the components of the sanitary napkin 20 are all gathered in along the flap transverse centerline $t_1$ (shown best in FIG. 10) while the portions of the components of the sanitary napkin spaced longitudinally away from the flap transverse centerline $t_1$ are gathered in to a lesser extent the farther they are spaced longitudinally away from the flap transverse centerline $t_1$. (Note that the cross-section of FIG. 10 is not taken through the zones of differential extensibility 50).

The folding or pleating of the sanitary napkin 20 also forms a hump 92 in the center of the main body portion 22. This hump 92 (although not necessarily drawn to scale in the drawing figures) is preferably made of such a size and shape that it is capable of fitting in the space between the wearer's labia.

In the embodiment shown in FIGS. 9–11, the pleated section of the sanitary napkin 20 (or hump) is gathered in and restrained by a pad restraint 94. The pad restraint 94 is preferably relatively inextensible so that it provides the desired zones of differential extensibility 50 in the corner regions 52 of the sanitary napkin 20. The pad restraint 94 may be in direct contact with the gathered in portions that form the hump, or it may bridge the hump. In the latter case, the pad restraint 94 may extend outward as far as the proximal edges 32 of the flaps and restrain the gathered in portions laterally outside the hump.

The pad restraint 94 can be made of any suitable material. Some non-limiting examples of suitable materials include paper (provided the same is not located where it can be wetted), tapes, nonwoven materials, and pieces of polyethylene film. The pad restraint 94 can also include any type of restraint described above as being suitable for the flap pleat restraint 66, and vice versa.

The sanitary napkin 20 of the present invention, as shown in FIGS. 9–11, can also have optional elastics 96 on or adjacent its flaps 24. In a preferred embodiment, the elastics 96 are located along the lines of juncture 30 adjacent the center portion 27 of the flaps 24. These elastics 96 are attached to the sanitary napkin 20 (preferably on the backsheet 42) in an elastically contractible condition. The elastics 96 assist the unrestrained pleated portions of the sanitary napkin 20 in opening so that the pleats are fully effective. The zones of differential extensibility 50 created in such an embodiment are still considered to be "elasticless." The elastics 96 are not used to gather in portions of the sanitary napkin to create the zones of differential extensibility 50, only to assist the unrestrained pleated portions in opening.

Similarly positioned elastics can be used for the same purpose in the other sanitary napkin embodiments described herein. The use of elastics 96 in the embodiment shown in FIGS. 9–11, however, is particularly important because it opens the unrestrained pleated portion of the napkin 20 prior to the attachment of the sanitary napkin 20 to the wearer's undergarments with the central pad adhesive 54. (If the elastics 96 were not used, the central pad adhesive 54 may tend to remain in the form of two parallel strips rather than two concave inwardly oriented strips as shown in FIGS. 9 and 11. If the strips of adhesive are parallel when they are attached to the wearer's undergarments, the effect of pleating and the gathering in the restrained portion of sanitary napkin 20 would be negated.)

Figure 12:
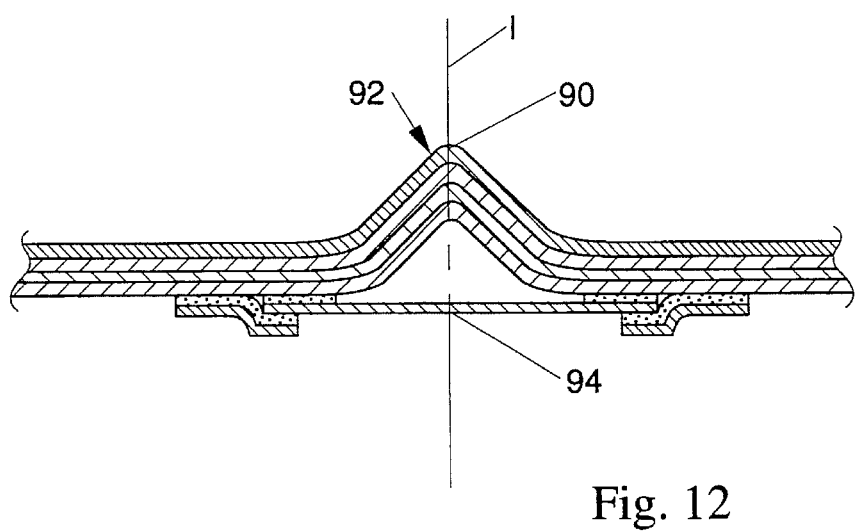
FIG. 12 is a simplified transverse cross-sectional view of another alternatively preferred sanitary napkin embodiment of the present invention in which the main body portion is folded only once.

FIG. 12 shows an alternative embodiment of the sanitary napkin 20 of the present invention in which the sanitary napkin 20 is folded or pleated only along one longitudinal line 90. In this case, the fold line 90 should, preferably, run along the principal longitudinal centerline 1.

Figure 13:
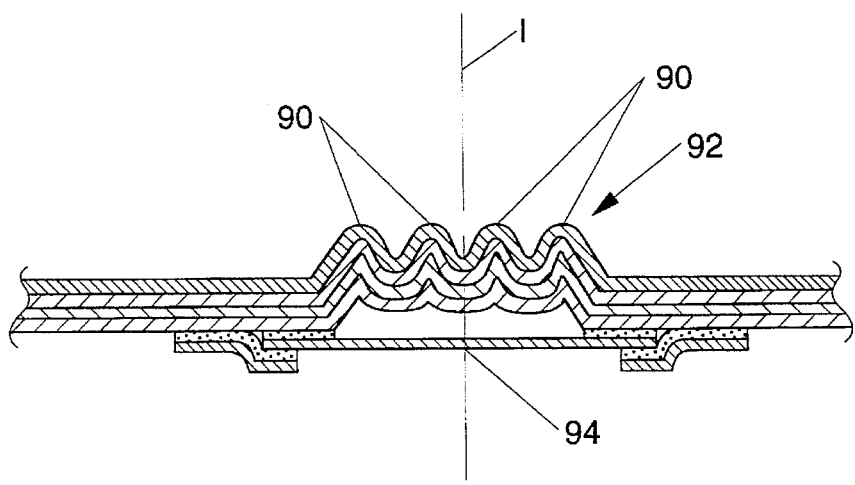
FIG. 13 is a simplified transverse cross-sectional view of another alternatively preferred sanitary napkin embodiment of the present invention in which the main body portion contains multiple folds.

FIG. 13 shows an alternative embodiment of the sanitary napkin 20 in which the sanitary napkin 20 is folded or pleated along a plurality of fold lines 90. In this case, the fold lines 90 are centered about the principal longitudinal centerline 1.

It should be apparent to one skilled in the art that in still other alternative embodiments, the flaps 24 (rather than the main body portion 22) could be provided with a single fold or multiple folds. For instance, the flaps 24 could be provided with folds similar to the folds through the entire pad shown in FIGS. 12 and 13. It is also apparent that in other alternative embodiments, the zones of differential extensibility 50 of the sanitary napkin 20, rather than being integral with the less extensible first portions of the sanitary napkin 20, could comprise separate pieces of material (such as separate slack material, or ring rolled, corrugated or pleated material) associated with the sanitary napkin.

Figure 16:
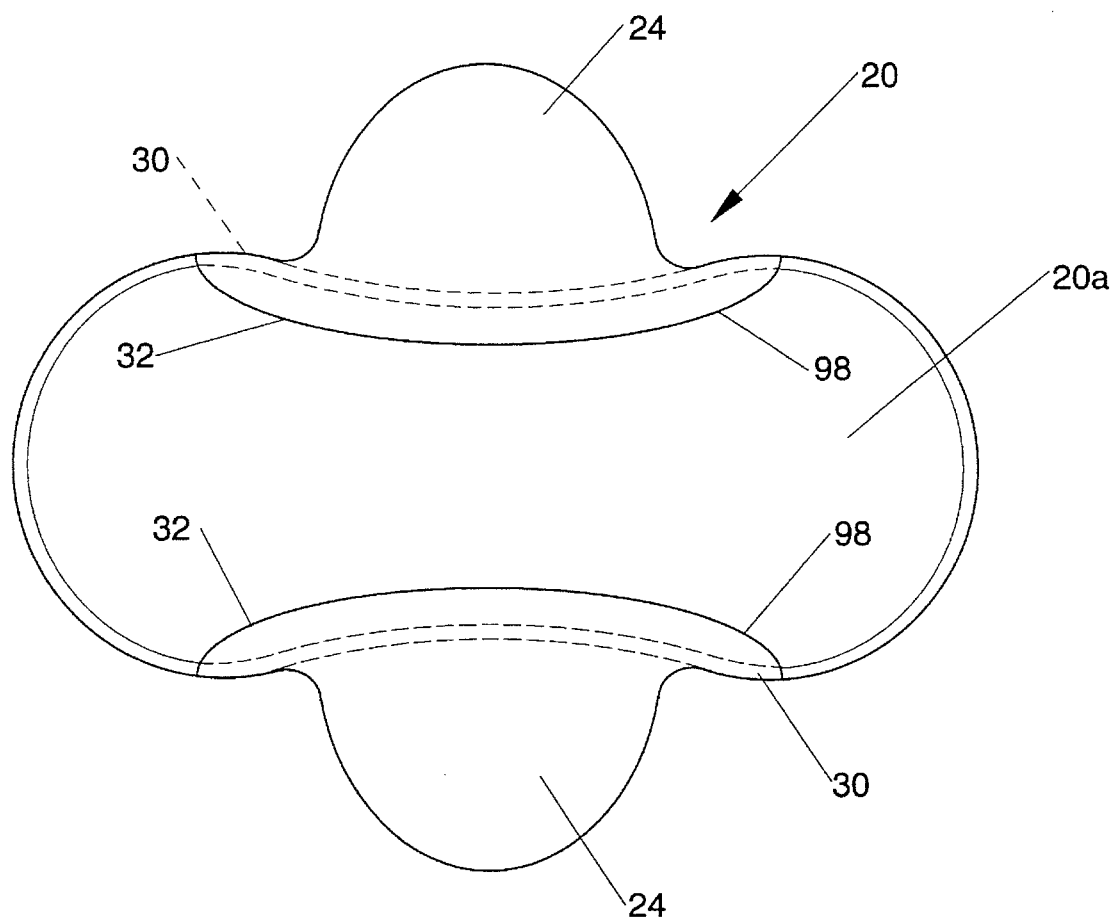
FIG. 16 is a top plan view of a sanitary napkin having flaps provided with an optional barrier feature.

FIG. 16 shows an alternative embodiment in which the sanitary napkin 20 is provided with a barrier 98 along the proximal edges 32 of the flaps 24. The barrier 98 stands up to serve as a wall to retain exudates flowing in the transverse direction toward the flaps 24 (shown in the flap 24 located near the top of the sheet containing FIG. 16). The barrier 98 may stand up before (and after) the sanitary napkin is placed in the wearer's undergarments, or it may initially lie relatively flat against the topsheet and use the forces exerted by folding of the flaps down under the wearer's undergarments to stand up. In other alternative embodiments, the barrier 98 may have its ends tacked down near the ends of the junctures so that it slants inwardly during use rather than standing straight up.

The barrier 98 may be provided on most of the embodiments described herein. (The barrier may also be provided on other sanitary napkin embodiments. For instance, the flaps of the sanitary napkin 20 shown are completely extensible. In addition, the sanitary napkin could even be provided with such a barrier 98 if it did not have flaps 24.) The barrier 98 may be constructed in any suitable manner, FIG. 16 shows one preferred construction in which the barrier 98 is formed by providing flaps 24 that comprise non-integral (or separate) elements. The barrier 98 is formed by providing these flap elements with an extension of excess material inboard of the junctures 30. The barrier 98 may be made of the same material as the remainder of the flaps 24. Alternatively, it may (and/or the portions of the flaps adjacent the barrier) may be made of a stiffer material to aid the barrier in standing up.

In still other alternative embodiments, the sanitary napkin could be provided with additional components. For instance, the sanitary napkin could be provided with the wet-laid tissue and/or the liquid permeable wipe acquisition sheet described in greater detail in U.S. Pat. No. 5,009,653 issued to Osborn. In addition, such sanitary napkins could be provided with additional types of stress relief means such as those described in U.S. Pat. No. 4,917,697 at various locations around the periphery of the sanitary napkin.

Thus, the present invention provides a sanitary napkin having flaps and zones of differential extensibility to provide an improved stress relief means for relieving the stresses that develop in the flaps when the flaps are folded down and under a wearer's undergarment.

While particular embodiments of the present invention have been illustrated and described, it would be obvious to those skilled in the art that various other changes and modifications can be made without departing from the spirit and scope of the invention.

What is claimed is:

1. The absorbent article for wearing in a wearer's undergarment which has a crotch region with a pair of side edges, said absorbent article having a principal longitudinal centerline that is oriented in a longitudinal direction, and a principal transverse centerline that is oriented in a transverse direction, said absorbent article comprising:

a main body portion having two spaced apart longitudinal edges, two spaced apart transverse edges, and laterally outermost portions, said main body portion comprising a liquid pervious topsheet, a liquid impervious backsheet joined to said topsheet, and an absorbent core positioned between said topsheet and said backsheet;

a pair of flaps at least partially around for folding along the side edges of the wearer's undergarment, said flaps being joined to said main body portion, one of said flaps extending laterally outward beyond the laterally outermost portions of said main body portion, said flaps having a flap transverse centerline and distal edges, said flaps comprising first portions of said flaps that are located along said flap transverse centerline, and second portions of said flaps, at least parts of which are spaced longitudinally away from said flap transverse centerline, wherein said second portions of said flaps spaced longitudinally away from said flap transverse centerline comprise at least one zone of differential extensibility having a greater range of extensibility outward in a generally transverse direction than said first portions of said flaps located along said flaps transverse centerline, said zone of differential extensibility comprising corrugated portions of said flaps which have ridges and valleys that are oriented at an angle relative to the principal longitudinal centerline.

2. The absorbent article for wearing in a wearer's undergarment which has a crotch region with a pair of side edges, said absorbent article having a principal longitudinal centerline that is oriented in a longitudinal direction, and a principal transverse centerline that is oriented in a transverse direction, said absorbent article comprising:

a main body portion having two spaced apart longitudinal edges, two spaced apart transverse edges, said main body portion comprising a liquid pervious topsheet, a liquid impervious backsheet joined to said topsheet, and an absorbent core positioned between said topsheet and said backsheet;

a pair of flaps for folding at least partially around the side edges of the wearer's undergarment, said flaps being joined to said main body portion, one of said flaps extending laterally outward beyond each of said longitudinal edges of said main body portion, said flaps having a flap transverse centerline and distal edges, said flaps comprising first portions of said flaps that are located along said flap transverse centerline, and second portions of said flaps that are spaced longitudinally away from said flap transverse centerline, wherein said second portions of said flaps spaced longitudinally away from said flap transverse centerline comprise at least one zone of differential extensibility having a greater range of extensibility outward in a generally transverse direction than said first portions of said flaps located along said flaps transverse centerline, said zone of differential extensibility comprising corrugated portions of said flaps which have generally longitudinally-oriented ridges and valleys.

3. The absorbent article of claim 2 wherein at least parts of said corrugated portions of said flaps are located at the distal edges of said flaps.

4. The absorbent article of claim 2 wherein when said flaps are folded around the side edges of a wearer's undergarment, the distal edges of said flaps will intersect with the side edges of the wearer's undergarment, and said corrugated portions of said flaps are located at least in the regions where the distal edges of the flaps intersect with the edges of the wearer's undergarment.

5. The absorbent article of claim 2 wherein said flaps extend outward from a juncture with said main body portion, and said corrugated portions of said flaps begin at a point located between the area of the flap transverse centerline and a point about 1.5 centimeters longitudinally outward from said flap transverse centerline and are bounded by the juncture on one side and the distal edge of the flap on another side.

6. The absorbent article of claim 5 wherein said corrugated portions of said flaps have a boundary that defines a three-sided figure in plan view.

7. The absorbent article of claim 2 wherein at least parts of said corrugated portions of said flaps are located along the entire juncture of said flaps.

8. The absorbent article of claim 2 wherein said main body portion has a laterally outermost portion, and said flaps extend laterally outward beyond the laterally outermost portion of said main body portion.

* * * * *